(12) United States Patent
Beard et al.

(10) Patent No.: US 6,787,535 B2
(45) Date of Patent: Sep. 7, 2004

(54) INDOLE DERIVATIVES WITH 5HT6 RECEPTOR AFFINITY

(75) Inventors: Colin Charles Beard, Palo Alto, CA (US); Robin Douglas Clark, Palo Alto, CA (US); Lawrence Emerson Fisher, Mountain View, CA (US); Ralph New Harris, III, Redwood City, CA (US); David Bruce Repke, Milpitas, CA (US); David George Putman, Saratoga, CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 28 days.

(21) Appl. No.: 10/164,660

(22) Filed: Jun. 6, 2002

(65) Prior Publication Data

US 2003/0073700 A1 Apr. 17, 2003

Related U.S. Application Data

(60) Provisional application No. 60/340,212, filed on Dec. 13, 2001, and provisional application No. 60/296,705, filed on Jun. 7, 2001.

(51) Int. Cl.[7] .............. A61K 31/33; A61K 31/495; A61K 31/405; C07D 403/00; C07D 209/04
(52) U.S. Cl. ............ 514/183; 514/254.09; 514/415; 544/366; 544/358; 544/373; 548/452; 548/469; 548/511; 548/503
(58) Field of Search ............... 514/183, 415, 514/254.09; 544/366, 358, 373; 548/452, 469, 511, 503

(56) References Cited

U.S. PATENT DOCUMENTS

6,187,805 B1 * 2/2001 Pineiro et al. .............. 514/415

FOREIGN PATENT DOCUMENTS

| EP | 0941994 A1 | 9/1999 |
| WO | WO 96/03400 A1 | 2/1996 |
| WO | WO 98/27081 A1 | 6/1998 |
| WO | 9850358 * | 11/1998 |
| WO | WO 01/32660 A1 | 5/2001 |

OTHER PUBLICATIONS

Kelley et al, PubMed Abstract 12117573, also cited as Physiol. Behav.,76/3,365–77(2002).*

Chabrier et al, PubMed Abstract 10442086, also cited as Cell.Mol.Life SDci.,55/8–9, 1029–35(1999).*

Meltzer HV, PubMed Abstract 7583621, also cited as Clin. Neurosci.,3/2,64–75(1995).*

Monsma, Jr., Frederick J., et al., "Cloning and Expression of a Novel Serotonin Receptor with High Affinity for Tricyclic Psychotropic Drugs," *Molecular Pharmacology*, 1993, 43:320–327, The American Society for Pharmacology and Experimental Therapeutics.

Isaac, Methvin et al., "6–Bicyclopiperazinyl–1–arylsulfonylindoles and 6–Bicyclopiperidinyl–1–arylsulfonylindoles Derivatives as Novel, Potent, andSelective 5–HT$_6$ Receptor Antagonists," *Bioorganic & Medicinal Chemistry Letters*, (2000), pp. 1719–1721, vol. 10, Pergamon.

* cited by examiner

*Primary Examiner*—Mukund Shah
*Assistant Examiner*—Sudhaker B. Patel
(74) *Attorney, Agent, or Firm*—Robert C. Hall

(57) ABSTRACT

This invention relates to compounds which have generally 5-HT6 receptor affinity and which are represented by Formula I:

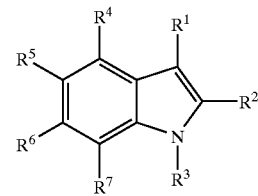

Formula I

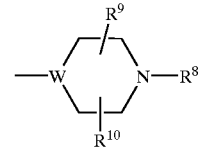

Formula B wherein one of $R^5$, $R^6$ or $R^7$ is a group of general Formula B, wherein W is a —CH— group or a nitrogen atom, and the other substituents are as defined herein; or individual isomers, racemic or non-racemic mixtures of isomers, or pharmaceutically acceptable salts or solvates thereof. The invention further relates to pharmaceutical compositions containing such compounds, methods for their use as therapeutic agents, and methods of preparation thereof.

32 Claims, No Drawings

INDOLE DERIVATIVES WITH 5HT6 RECEPTOR AFFINITY

CROSS REFERENCE TO RELATED APPLICATIONS

Pursuant to 35 U.S.C. §119(e), this application claims priority to the filing dates of the U.S. Provisional Patent Applications Serial No. 60/296,705, filed Jun. 7, 2001, and Ser. No. 60/340,212, filed Dec. 13, 2001, which are incorporated herein by reference in their entirety.

FIELD OF THE INVENTION

This invention relates to new indole derivatives with 5-HT6 receptor affinity, and associated pharmaceutical compositions, methods for use as therapeutic agents, and methods of preparation thereof.

BACKGROUND OF THE INVENTION

The actions of the neurotransmitter 5-hydroxytryptamine (5-HT) as a major modulatory neurotransmitter in the brain, are mediated through a number of receptor families termed 5-HT1, 5-HT2, 5-HT3, 5-HT4, 5-HT5, 5-HT6, and 5-HT7. Based on a high level of 5-HT6 receptor mRNA in the brain, it has been stated that the 5-HT6 receptor may play a role in the pathology and treatment of central nervous system disorders. In particular, 5-HT6 selective ligands have been identified as potentially useful in the treatment of certain CNS disorders such as Parkinson's disease, Huntington's disease, anxiety, depression, manic depression, psychoses, epilepsy, obsessive compulsive disorders, migraine, Alzheimer's disease (enhancement of cognitive memory), sleep disorders, feeding disorders such as anorexia and bulimia, panic attacks, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain gastrointestinal (GI) disorders such as functional bowel disorder. (See for ex. B. L. Roth et al., *J. Pharmacol. Exp. Ther.,* 1994, 268, pages 1403–14120, D. R. Sibley et al., *Mol. Pharmacol.,* 1993, 43, 320–327, A. J. Sleight et al., Neurotransmission, 1995, 11, 1–5, and A. J. Sleight et al. *Serotonin ID Research Alert,* 1997, 2 (3), 115–8). Furthermore, the effect of 5-HT6 antagonist and 5-HT6 antisense aligonucleotides to reduce food intake in rats has been reported (Br J Pharmac. 1999 Suppl 126, page 66 and J Psychopharmacol Suppl A64 1997, page 255).

SUMMARY OF THE INVENTION

This invention relates to compounds comprising Formula I:

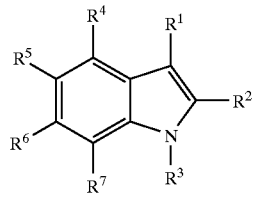

Formula I wherein:

$R^1$ is —$S(O)_{0-2}$—A, —C(O)—A, or —$(CH_2)_{0-1}$—A, wherein A is aryl or heteroaryl, and said aryl or heteroaryl are each independently in each occurrence optionally substituted with one or more groups selected from hydroxy, cyano, lower alkyl, lower alkoxy, thioalkyl, halo, haloalkyl, hydroxyalkyl, nitro, alkoxycarbonyl, alkylcarbonyl, alkylsulfonyl, haloalkylsulfonyl, amino, alkylamino, dialkylamino, alkylaminocarbonyl, alkylcarbonylamino, alkylaminosulfonyl, and alkylsulfonylamino;

$R^2$ is selected from hydrogen, $C_{1-6}$-alkyl, $C_{1-6}$-alkoxy, and $C_{1-6}$-alkylthio;

$R^3$ is selected from hydrogen and $C_{1-6}$-alkyl;

$R^4$ is selected from hydrogen, halogen, $C_{1-6}$-alkyl, $C_{1-6}$-alkoxy, $C_{1-6}$-alkylthio, haloalkyl, cyano, and alkylcarbonyl; and one of $R^5$, $R^6$ or $R^7$ is a group of general Formula B, wherein W is a —CH— group or a nitrogen atom, and $R^8$, $R^9$ and $R^{10}$ are each independently selected from hydrogen, $C_{1-10}$-alkyl and benzyl, or $R^8$ and $R^9$ together may form a $C_3$-$C_4$ alkylene;

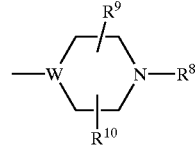

Formula B and the others are each independently in each occurrence selected from hydrogen, halogen, $C_{1-6}$-alkyl, $C_{1-6}$-alkoxy, $C_{1-6}$-alkylthio, haloalkyl, cyano, and alkylcarbonyl;

or individual isomers, racemic or non racemic mixtures of isomers, prodrugs, or pharmaceutically acceptable salts or solvates thereof.

In another aspect, the invention relates to pharmaceutical compositions containing a therapeutically effective amount of at least one compound of Formula I, or individual isomers, racemic or non-racemic mixtures of isomers, or pharmaceutically acceptable salts or solvates thereof, in admixture with at least one suitable carrier.

In another aspect, this invention relates to a method of treatment of a disease in a mammal treatable by administration of a compound of Formula I having a selective affinity for the 5-HT6 receptor, in particular a method of treatment in a subject having a disease state comprising Alzheimer's disease, central nervous disorders, such as for example, psychoses, schizophrenia, manic depressions, neurological disorders, Parkinson's disease, amyotrophic lateral sclerosis and Huntington's disease. In another aspect, this invention relates to a method of treatment in a subject having a gastrointestinal disease comprising irritable bowel syndrome (IBS).

In another aspect, the invention relates to a process which comprises:

i) reacting a compound having a general Formula 4

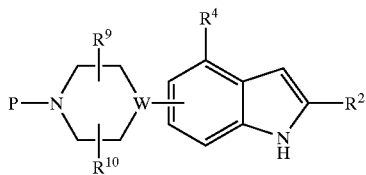

wherein P is a protecting group and $R^2$, $R^4$, $R^9$, and $R^{10}$ are as defined herein, with a compound of general formula $(A-S)_2$, wherein A is aryl or heteroaryl, to provide an adduct 4a

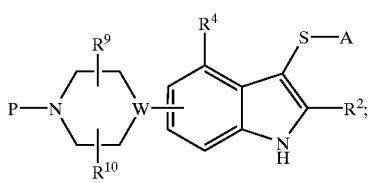

ii) oxidation of the sulfur atom of 4a;
iii) optional alkylation of the nitrogen of the indole group of oxidized 4a; and
iv) removal of the protecting group P;, to provide a compound of the general Formula I,

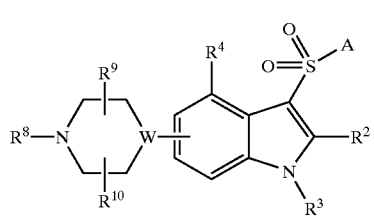

wherein $R^8$ is hydrogen, and A, $R^2$, $R^3$, $R^4$, $R^9$, and $R^{10}$ are as defined in the summary of the invention, and
v) optional alkylation of the nitrogen of the piperazine or piperidine group; to provide a compound of the general Formula I, wherein $R^8$ is $C_{1-10}$-alkyl, and A, $R^2$, $R^3$, $R^4$, $R^9$, and $R^{10}$ are as defined in the Summary of the Invention.

In another embodiment, the invention further relates to a process which comprises:
i) reacting a compound having a general Formula 4

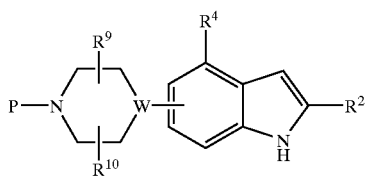

wherein P is a protecting group and $R^2$, $R^4$, $R^9$ and $R^{10}$ are as defined herein, with a compound of general formula $(A-S)_2$, wherein A is aryl or heteroaryl,
ii) optional alkylation of the nitrogen of the indole group,
iii) removing the protecting group P;

to provide a compound of the general Formula I,

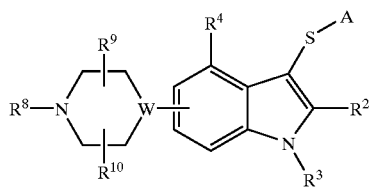

wherein $R^8$ is hydrogen, and A, $R^2$, $R^3$, $R^4$, $R^9$, and $R^{10}$ are as defined in the summary of the invention, and
iv) optional alkylation of the nitrogen of the piperazine or piperidine group to provide a compound of the general Formula I, wherein $R^8$ is $C_{1-10}$-alkyl, and A, $R^2$, $R^3$, $R^4$, $R^9$, and $R^{10}$ are as defined in the Summary of the Invention.

In another embodiment, the invention further relates to a process which comprises:
i) reacting a 1-halo-2-nitrobenzene with a halomethanesulfonyl benzene to provide a 1-benzenesulfonylmethyl-2-nitrobenzene;
ii) amination of the 1-benzenesulfonylmethyl-2-nitrobenzene with a 1-alkylpiperazine to provide a piperazinylated nitrobenzene;
iii) reduction of the nitro group of the piperazinylated nitrobenzene, and
iv) addition of an orthoformate, followed by cyclization to yield a compound of Formula 18a,

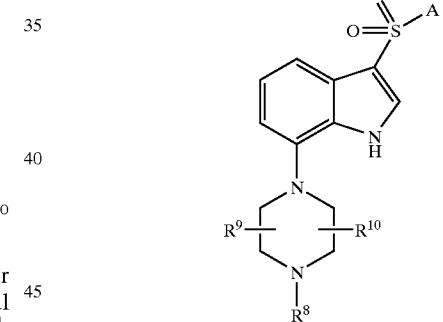

wherein $R^8$ is $C_{1-10}$-alkyl and A, $R^9$, and $R^{10}$ are as defined in the summary of the invention.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Alkyl" means a monovalent linear or branched saturated hydrocarbon radical, consisting solely of carbon and hydrogen atoms, having from one to twelve carbon atoms inclusive, unless otherwise indicated. Examples of alkyl radicals include, but are not limited to, methyl, ethyl, propyl, isopropyl, isobutyl, sec-butyl, tert-butyl, pentyl, n-hexyl, octyl, dodecyl, and the like. "Alkyl" also means a cyclic or a combination of linear or branched, and cyclic saturated hydrocarbon radical consisting solely of carbon and hydrogen atoms, having from one to twelve carbon atoms inclusive, unless otherwise indicated. Examples of such alkyl radicals include but are not limited to, cyclopropyl, cyclopropylmethyl, cyclohexyl, cyclopropylethyl and the like.

"Lower alkyl" means a monovalent linear or branched saturated hydrocarbon radical, consisting solely of carbon and hydrogen atoms, having from one to six carbon atoms inclusive, unless otherwise indicated. Examples of lower alkyl radicals include, but are not limited to, methyl, ethyl, propyl, isopropyl, sec-butyl, tert-butyl, n-butyl, n-pentyl, n-hexyl, and the like.

"Alkylene" means a divalent linear or branched saturated hydrocarbon radical, consisting solely of carbon and hydrogen atoms, having from one to six carbons inclusive, unless otherwise indicated. Examples of alkylene radicals include, but are not limited to, methylene, ethylene, propylene, 2-methyl-propylene, butylene, 2-ethylbutylene, and the like.

"Alkoxy" means a radical —O-R, wherein R is a lower alkyl radical as defined herein. Examples of alkoxy radicals include, but are not limited to, methoxy, ethoxy, isopropoxy, and the like.

"Alkylthio" or "alkylsulfanyl" means a radical —SR, wherein R is a lower alkyl radical as defined herein. Examples of alkylthio radicals include, but are not limited to, methylthio, butylthio, and the like.

"Alkylsulfonyl" means a radical —SO$_2$R, wherein R is a lower alkyl radical as defined herein. Examples of alkylsulfonyl radicals include, but are not limited to, methylsulfonyl, ethylsulfonyl, and the like.

"Aryl" means a monovalent cyclic aromatic hydrocarbon radical consisting of one or more fused rings in which at least one ring is aromatic in nature, which can optionally be substituted with hydroxy, cyano, lower alkyl, lower alkoxy, thioalkyl, halo, haloalkyl, hydroxyalkyl, nitro, alkoxycarbonyl, amino, alkylamino, dialkylamino, aminocarbonyl, carbonylamino, aminosulfonyl, sulfonylamino, and/or trifluoromethyl, unless otherwise indicated. Examples of aryl radicals include, but are not limited to, phenyl, naphthyl, biphenyl, indanyl, anthraquinolyl, and the like. Examples of substituted aryl radicals include but are not limited to fluorophenyl, chlorophenyl, dichlorophenyl, trifluoromethylphenyl, tolyl, and the like.

"Heteroaryl" means a monovalent aromatic carbocyclic radical having one or more rings incorporating one, two, or three heteroatoms within the ring (chosen from nitrogen, oxygen, or sulfur) which can optionally be substituted with hydroxy, cyano, lower alkyl, lower alkoxy, thioalkyl, halo, haloalkyl, hydroxyalkyl, nitro, alkoxycarbonyl, amino, alkylamino, dialkylamino, aminocarbonyl, carbonylamino, aminosulfonyl, sulfonylamino and/or trifluoromethyl, unless otherwise indicated. Examples of heteroaryl radicals include, but are not limited to, imidazolyl, oxazolyl, thiazolyl, pyrazinyl, thiophenyl, furanyl, pyranyl, pyridinyl, quinolinyl, isoquinolinyl, benzofuryl, benzothiophenyl, benzothiopyranyl, benzimidazolyl, benzooxazolyl, benzothiazolyl, benzopyranyl, indazolyl, indolyl, isoindolyl, naphtyridinyl, and the like.

"Leaving group" means the group with the meaning conventionally associated with it in synthetic organic chemistry, i.e., an atom or group displaceable under alkylating conditions. Examples of leaving groups include, but are not limited to, halogen, alkyl- or arylsulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Amino-protecting group" means the protecting group that refers to those organic groups intended to protect the nitrogen atom against undesirable reactions during synthetic procedures and includes, but is not limited to, benzyl (Bnz), benzyloxycarbonyl (carbobenzyloxy, Cbz), p-methoxybenzyloxycarbonyl, p-nitrobenzyloxycarbonyl, tert-butoxycarbonyl (Boc), trifluoroacetyl, and the like. It is preferred to use either Boc or Cbz as the amino-protecting group because of the relative ease of removal, for example by acids in the case of Boc, e.g., trifluoroacetic acid or hydrochloric acid in ethyl acetate; or by catalytic hydrogenation in the case of Cbz.

"Optional" or "optionally" means that the subsequently described event or circumstance may but need not occur, and that the description includes instances where the event or circumstance occurs and instances in which it does not. For example, "optional bond" means that the bond may or may not be present, and that the description includes single, double, or triple bonds "Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive oxygen atoms present in the reactants. Acceptable protective groups for alcoholic or phenolic hydroxyl groups, which may be removed successively and selectively includes groups protected as acetates, haloalkyl carbonates, benzyl ethers, alkylsilyl ethers, heterocyclyl ethers, and methyl or alkyl ethers, and the like. Protective or blocking groups for carboxyl groups are similar to those described for hydroxyl groups, preferably tert-butyl, benzyl or methyl esters "Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

(1) acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, trifluoroacetic acid, and the like; or (2) salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, trifluoroacetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Prodrug" or "pro-drug" means a pharmacologically inactive form of a compound which must be metabolized in vivo, e.g., by biological fluids or enzymes, by a subject after administration into a pharmacologically active form of the compound in order to produce the desired pharmacological effect. Prodrugs of a compound of Formula I are prepared by modifying one or more functional group(s) present in the compound of Formula I in such a way that the modification(s) may be cleaved in vivo to release the parent compound. Prodrugs include compounds of Formula I wherein a hydroxy, amino, sulfhydryl, carboxy or carbonyl group in a compound of Formula I is bonded to any group that may be cleaved in vivo to regenerate the free hydroxyl, amino, sulfhydryl, carboxy or carbonyl group respectively. Examples of prodrugs include, but are not limited to, esters (e.g. acetate, dialkylaminoacetates, formates, phosphates, sulfates and benzoate derivatives) and carbamates of hydroxy functional groups (e.g. N,N-dimethylcarbonyl), esters of carboxyl functional groups (e.g. ethyl esters, morpholinoethanol esters), N-acyl derivatives (e.g. N-acetyl), N-Mannich bases, Schiff bases and enaminones of amino functional groups, oximes, acetals, ketals, and enol esters of ketones and aldehyde functional groups in compounds of Formula I, and the like.

The prodrug can be metabolized before absorption, during absorption, after absorption, or at a specific site. Although metabolism occurs for many compounds primarily in the liver, almost all other tissues and organs, especially the lung, are able to carry out varying degrees of metabolism. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site-specific delivery of the compound. Reference to a compound herein includes prodrug forms of a compound. Prodrugs are described in *The Organic Chemistry of Drug Design and Drug Action,* by Richard B. Silverman, Academic Press, San Diego, 1992. Chapter 8: "Prodrugs and Drug delivery Systems" pp.352–401; *Design of Prodrugs,* edited by H. Bundgaard, Elsevier Science, Amsterdam, 1985; *Design of Biopharmaceutical Properties through Prodrugs and Analogs,* Ed. by E. B. Roche, American Pharmaceutical Association, Washington, 1977; and *Drug Delivery Systems,* ed. by R. L. Juliano, Oxford Univ. Press, Oxford, 1980.

"Subject" means mammals and non-mammals. Mammals means any member of the Mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgement of the attending medical or veterinary practitioner, and other factors.

"Disease state" means any disease, condition, symptom, or indication.

Throughout the application the following abbreviations are used with the following meaning:

| | |
|---|---|
| Alk | Alkyl group |
| Boc | N-tert-butoxycarbonyl |
| m-CPBA | m-Chloroperbenzoic acid |
| DTB | Di-tert-butyldicarbonate |
| DMF | N,N-Dimethylformamide |
| DMFDMA | N,N-dimethylformamide dimethyl acetal |
| DMSO | Dimethylsulfoxide |
| L | Leaving group |
| Oxone ™ | Potassium peroxymonosulfate |
| P | Protective group |
| TFA | Trifluoroacetic acid |
| THF | Tetrahydrofuran |

Nomenclature

In general, the nomenclature used in this Application is based on AUTONOM™ v.4.0, a Beilstein Institute computerized system for the generation of IUPAC systematic nomenclature. However, because a strict adherence to these recommendations would result in the names changing substantially when only a single substituent is changed, compounds have been named in a manner that maintains consistency of nomenclature for the basic structure of the molecule.

For example, a compound of Formula I wherein $R^2$, $R^3$, $R^4$, $R^5$ and $R^6$ are hydrogen, $R^1$ is phenylsulfonyl, and $R^7$ is piperazinyl is named 3-benzenesulfonyl-7-piperazin-1-yl-1H-indole.

Preferred Compounds

While the broadest definition of this invention is set forth in the Summary of the Invention certain compounds of Formula I, or individual isomers, racemic or non-racemic mixtures of isomers, or pharmaceutically acceptable salts or solvates thereof, are preferred:

$R^1$ is —$S(O)_{0-2}$—A, wherein A is aryl or heteroaryl. Other preferred compounds are those wherein $R^1$ is preferably —S(O)$_{0-2}$—A, wherein A is phenyl optionally substituted with one or more substituents selected from C$_{1-6}$-alkyl, C$_{1-6}$-alkoxy, halogen and haloalkyl. Other preferred compounds are those wherein R$^1$ is preferably —S(O)$_2$—A, wherein A is phenyl optionally substituted with one or more substituents selected from C$_{1-6}$-alkyl, C$_{1-6}$-alkoxy, halogen and haloalkyl. Other preferred compounds are those wherein R$^1$ is preferably —S—A, wherein A is phenyl optionally substituted with one or more substituents selected from C$_{1-6}$-alkyl, C$_{1-6}$-alkoxy, halogen and haloalkyl.

In another preferred embodiment R$^1$ is preferably —S(O)$_{0-2}$—A, wherein A is heteroaryl, more preferably R$^1$—S(O)$_2$—A, wherein A is pyridinyl or benzothiazolyl.

R$^2$ and R$^3$ are preferably hydrogen or C$_{1-6}$-alkyl.

R$^4$ is preferably hydrogen.

R$^8$ is preferably hydrogen or C$_{1-10}$-alkyl, and R$^9$ and R$^{10}$ are preferably hydrogen.

In a preferred embodiment R$^7$ is a piperazinyl group of general Formula B, wherein W is a nitrogen atom, and R$^5$ and R$^6$ are hydrogen.

In another preferred embodiment R$^5$ is a piperazinyl group of general Formula B, wherein W is a nitrogen atom, and R$^5$ and R$^6$ are hydrogen.

Exemplary particularly preferred compounds, or individual isomers, racemic or non-racemic mixtures of isomers, or pharmaceutically acceptable salts or solvates thereof, comprise:

3-benzenesulfonyl-7-piperazin-1-yl-1H-indole;
3-benzenesulfonyl-1-methyl-7-piperazin-1-yl-1H-indole;
3-benzenesulfonyl-2-methyl-7-piperazin-1-yl-1H-indole;
3-(4-chlorobenzenesulfonyl)-2-methyl-7-piperazin-1-yl-1H-indole;
3-(4-methoxybenzenesulfonyl)-2-methyl-7-piperazin-1-yl-1H-indole;
3-benzenesulfonyl-5-piperazin-1-yl-1H-indole;
7-piperazin-1-yl-3-(pyridine-4-sulfonyl)-1H-indole;
7-piperazin-1-yl-3-(pyridine-2-sulfonyl)-1H-indole;
1-methyl-7-piperazin-1-yl-3-(pyridine-2-sulfonyl)-1H-indole;
3-benzenesulfonyl-7-(4-methyl-piperazin-1-yl)-1H-indole;
3-benzenesulfonyl-1-methyl-5-piperazin-1-yl-1H-indole;
3-(3,4-dichloro-benzenesulfonyl)-7-piperazin-1-yl-1H-indole;
2-(7-piperazin-1-yl-1H-indole-3-sulfonyl)-benzothiazole;
3-(4-fluoro-benzenesulfonyl)-2-methyl-7-piperazin-1-yl-1H-indole;
3-(4-fluoro-benzenesulfonyl)-7-piperazin-1-yl-1H-indole;
3-benzenesulfonyl-7-piperidin-4-yl-1H-indole;
7-piperazin-1-yl-3-(toluene-4-sulfonyl)-1H-indole;
3-(3,5-dichloro-benzenesulfonyl)-7-piperazin-1-yl-1H-indole;
3-(3-chloro-benzenesulfonyl)-7-piperazin-1-yl-1H-indole;
3-(2-chloro-benzenesulfonyl)-7-piperazin-1-yl-1H-indole;
7-piperazin-1-yl-3-(2-trifluoromethyl-benzenesulfonyl)-1H-indole;
1-methyl-7-piperazin-1-yl-3-(2-trifluoromethyl-benzenesulfonyl)-1H-indole;
3-(4-fluoro-benzenesulfonyl)-1-methyl-7-piperazin-1-yl-1H-indole;
1-methyl-7-piperazin-1-yl-3-(pyridine-2-sulfonyl)-1H-indole;
1-methyl-7-piperazin-1-yl-3-(3-trifluoromethyl-benzenesulfonyl)-1H-indole;
3-(2-chloro-benzenesulfonyl)-1-methyl-7-piperazin-1-yl-1H-indole;
3-(3-chloro-benzenesulfonyl)-1-methyl-7-piperazin-1-yl-1H-indole;
3-benzenesulfonyl-1-methyl-7-(4-methyl-piperazin-1-yl)-1H-indole;
3-(2,3-dichloro-phenylsulfanyl)-5-piperazin-1-yl-1H-indole;
3-(2,3-dichloro-benzenesulfonyl)-5-piperazin-1-yl-1H-indole;
3-(2,3-dichloro-benzenesulfonyl)-1-methyl-5-piperazin-1-yl-1H-indole;
1-methyl-5-piperazin-1-yl-3-(3-trifluoromethyl-benzenesulfonyl)-1H-indole;
5-piperazin-1-yl-3-(4-trifluoromethyl-benzenesulfonyl)-1H-indole;
3-(4-chloro-benzenesulfonyl)-5-piperazin-1-yl-1H-indole;
3-(3,5-dichloro-benzenesulfonyl)-5-piperazin-1-yl-1H-indole;
3-(3,5-dichloro-benzenesulfonyl)-1-methyl-5-piperazin-1-yl-1H-indole;
3-phenylsulfanyl-5-piperazin-1-yl-1H-indole;
3-(2-chloro-benzenesulfonyl)-5-piperazin-1-yl-1H-indole;
3-(4-fluoro-benzenesulfonyl)-5-piperazin-1-yl-1H-indole;
3-(4-fluoro-benzenesulfonyl)-1-methyl-5-piperazin-1-yl-1H-indole;
3-(2-chloro-benzenesulfonyl)-1-methyl-5-piperazin-1-yl-1H-indole;
3-(3,4-dichloro-benzenesulfonyl)-7-(4-methyl-piperazin-1-yl)-1H-indole;
3-(2-chloro-benzenesulfonyl)-7-(4-methyl-piperazin-1-yl)-1H-indole;
3-(3-chloro-benzenesulfonyl)-7-(4-methyl-piperazin-1-yl)-1H-indole;
3-(2,4-dichloro-benzenesulfonyl)-7-(4-methyl-piperazin-1-yl)-1H-indole;
3-(3,5-dichloro-benzenesulfonyl)-7-(4-methyl-piperazin-1-yl)-1H-indole;
7-(4-methyl-piperazin-1-yl)-3-(2-trifluoromethyl-benzenesulfonyl)-1H-indole; and
3-phenylsulfanyl-7-piperazin-1-yl-1H-indole.

General Synthetic Reaction Schemes

Compounds of the present invention may be made by the methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis;* Wiley & Sons: New York, 1991, Volumes 1–15; *Rodd's Chemistry of Carbon Compounds,* Elsevier Science Publishers, 1989, Volumes 1–5 and Supplementals; and *Organic Reactions,*

Wiley & Sons: New York, 1991, Volumes 1–40. The following synthetic reaction schemes are merely illustrative of some methods by which the compounds of the present invention may be synthesized, and various modifications to these synthetic reaction schemes may be made and will be suggested to one skilled in the art having referred to the disclosure contained in this Application.

The starting materials and the intermediates of the synthetic reaction schemes may be isolated and purified if desired using conventional techniques, including but not limited to filtration, distillation, crystallization, chromatography, and the like. Such materials may be characterized using conventional means, including physical constants and spectral data.

Unless specified to the contrary, the reactions described herein preferably take place at atmospheric pressure over a temperature range from about −78° C. to about 150° C., more preferably from about 0° C. to about 125° C., and most preferably and conveniently at about room (or ambient) temperature, e.g., about 20° C.

Scheme A

Scheme A describes methods of preparing piperazinyl indoles.

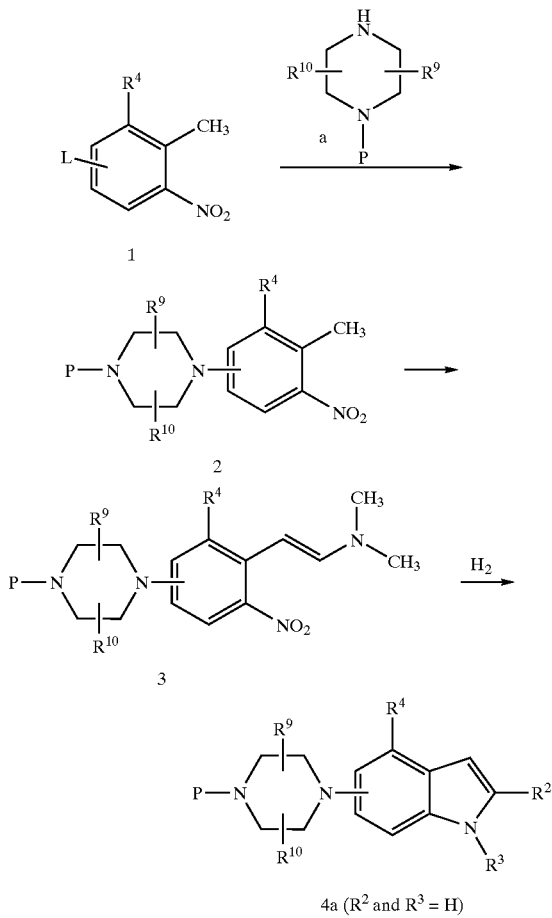

Ortho-nitrotoluenes substituted with a protected piperazinyl group on the phenyl ring can be converted to 2-unsubstituted indoles (4a, $R^2$ and $R^3$=H, P is a protecting group) via the Leimgruber-Batcho synthesis as described in *Organic Synthesis* Collective Volume 7, page 34 and in *Heterocycles*, 22, 195 (1984). The ortho-nitrotoluene (2) is condensed with N,N-dimethylformamide dimethyl or diethyl acetal, tert-butoxy-bis(dimethylamino)methane, and the like in a suitable solvent such as DMF, optionally in the presence of an added amine such as pyrrolidine to afford the dialkylaminonitrostyrene (3). Reduction of the nitrostyrene to the indole (4a, $R^2$ and $R^3$=H) can be affected by a variety of methods such as catalytic hydrogenation, transfer hydrogenation, or by chemical reducing agents such as titanium trichloride, iron or zinc metal.

1-Protected 4-piperazinyl nitrotoluene precursors for the Batcho-Leimgruber indole synthesis can be prepared by nucleophilic displacement of a nitrobenzene with a leaving group such as a halo or trifluoromethanesulfonyloxy with a suitably 1-protected piperazine of general formula a, wherein P is a protecting group, as described in *Synthesis*, 1145 (1990) for displacement of 2-trifluoromethanesulfonyloxy nitrobenzene with 1-benzylpiperazine. Other suitable protecting groups include N-tert-butoxycarbonyl (Boc), carbobenzyloxy (Cbz), carbethoxy, acetyl, benzoyl, and formyl groups.

Alternatively, piperazine can be used in the displacement as described in *J. Med. Chem.*, 42, 4794 (1999) for the preparation of 1-(2-nitrophenyl)piperazine and the resulting nitrophenyl piperazine can be protected by conventional methods such as by treatment with di-tert-butyldicarbonate to afford the Boc derivative.

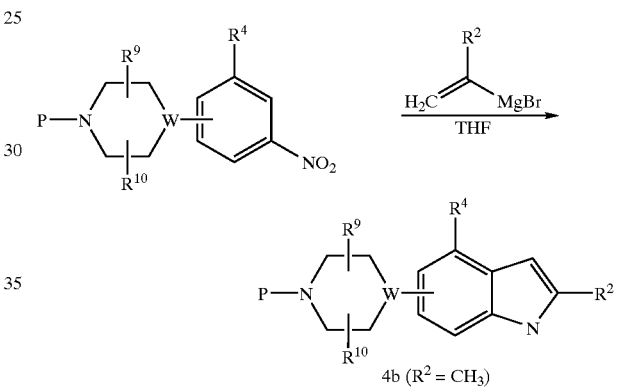

Piperazinylindoles or piperidinylindoles can also be prepared by the Bartoli indole synthesis which is described in *Tetrahedron Letters*, 30, 2129 (1989). A suitably protected 2-piperazinyl or 2-piperidinyl nitrobenzene is treated with a vinyl Grignard reagent in THF to afford the indole (4b) in a single step. 2-Alkyl substituted indoles, which are not available via the Leimgruber-Batcho synthesis, can be prepared by this route.

Piperazinylindoles can also be prepared from the corresponding aminoindole by reaction of the amino group with bis-chloroethylamine or a suitably protected derivative thereof as is well known in the art. For example, preparation of 7-(1-piperazinyl)indole by treatment of 7-aminoindole with bis-chloroethylamine is described in WO 94/15919.

Piperazinylindoles can also be prepared from ortho-nitrophenylacetonitriles as described for the preparation of 7-(4-carbethoxypiperazin-1-yl)indole in UK Patent Application GB 2097790.

Piperazinylindoles can also be prepared from the corresponding bromoindole by Palladium-catalyzed coupling with a suitably protected piperazine, such as Boc-piperazine (Buchwald reaction).

Piperdinylindoles can be prepared by conversion of a suitably protected haloindole to the lithio derivative, followed by condensation with a suitably protected 4-piperidone, and subsequent dehydration and reduction of the olefin.

Scheme B

Scheme B describes methods of preparing compounds of Formula I wherein $R^1$, $R^2$, $R^3$, $R^4$, $R^5$, $R^6$, $R^7$, $R^8$, $R^9$, $R^{10}$, and A are as defined in the Summary of the Invention.

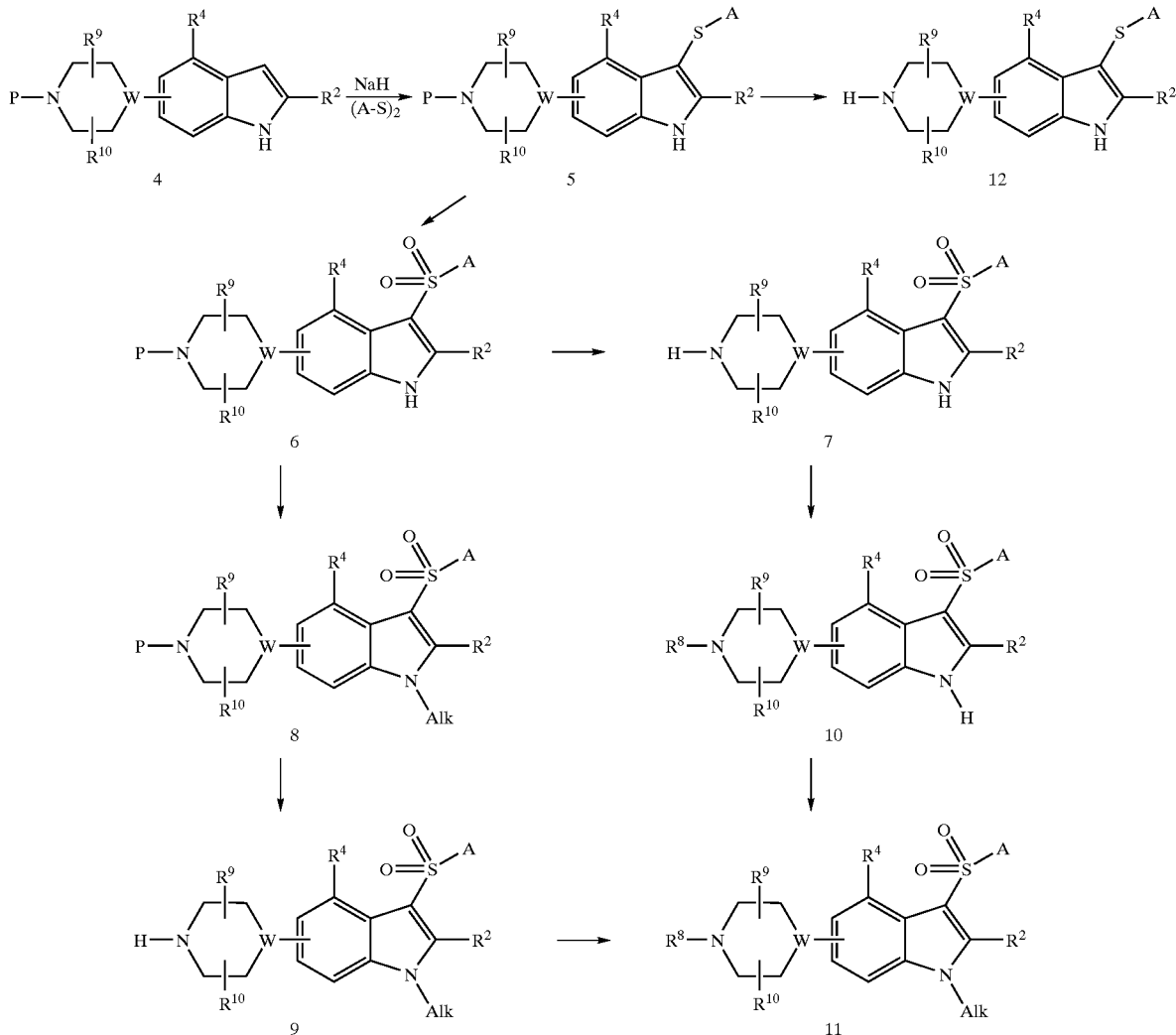

3-Aryl- or 3-heteroaryl sulfanyl indoles of general Formula (5), wherein P is a protecting group and W is —CH— or N, are prepared by reaction of the indole sodium salt with an aryl or a heteroaryl disulfide as described in *Synthesis* 480 (1988). Aryl or heteroaryl disulfides are commercially available or can be easily prepared by oxidation of the corresponding aryl or heteroaryl thiol by means well known to those skilled in the art.

Removal of the protecting group (P) from the piperazine or piperidine of general Formula (5) under standard conditions can afford compounds of Formula (12).

Oxidation of the aryl or heteroaryl sulfanyl group to the aryl or heteroaryl sultonyl group can be accomplished with a suitable oxidizing agent such as potassium peroxymonosulfate (Oxone™), 3-chloroperoxybenzoic acid, peracetic acid, hydrogen peroxide, ozone and the like. It will be appreciated that with some of these oxidizing agents oxidation of the piperazinyl nitrogen may also occur to give the N-oxide. In these cases, reduction of the N-oxide back to the parent piperazine of general Formula (6) can be effected with a suitable reducing agent such as hydrogen (catalytic hydrogenation), triphenylphosphine and the like.

Removal of the protecting group (P) from the piperazine or piperidine of general Formula (6) is accomplished under standard conditions, e.g., cleavage of the Boc group by treatment with a strong acid such as trifluoroacetic in a suitable solvent such as dichloromethane or hydrochloric acid in a suitable solvent such as water, ethanol or ethyl acetate, to afford compounds of general Formula (7).

1-Substituted derivatives of general Formula (8), wherein Alk is an alkyl group, are prepared by alkylation of the sodium salt of the parent indole of general Formula (6) with a suitable alkylating agent such as an alkyl halide or sulfonate in a suitable solvent such as tetrahydrofuran or DMF, to afford compounds of general Formula (9).

Coupling of compounds of general Formula (7) or (9) with a carboxyaldehyde under reductive amination conditions can afford compounds (10) or (11) respectively, wherein $R^8$ is $C_{1-10}$-alkyl group.

Scheme C

Scheme C describes an alternative method of preparing a compound of Formula I wherein $R^1$ is —$SO_2$—A, and $R^8$ is $C_{1-10}$—alkyl, $R^2$, $R^3$, $R^4$, $R^5$, $R^6$ are hydrogen and A is as defined in the Summary of the Invention.

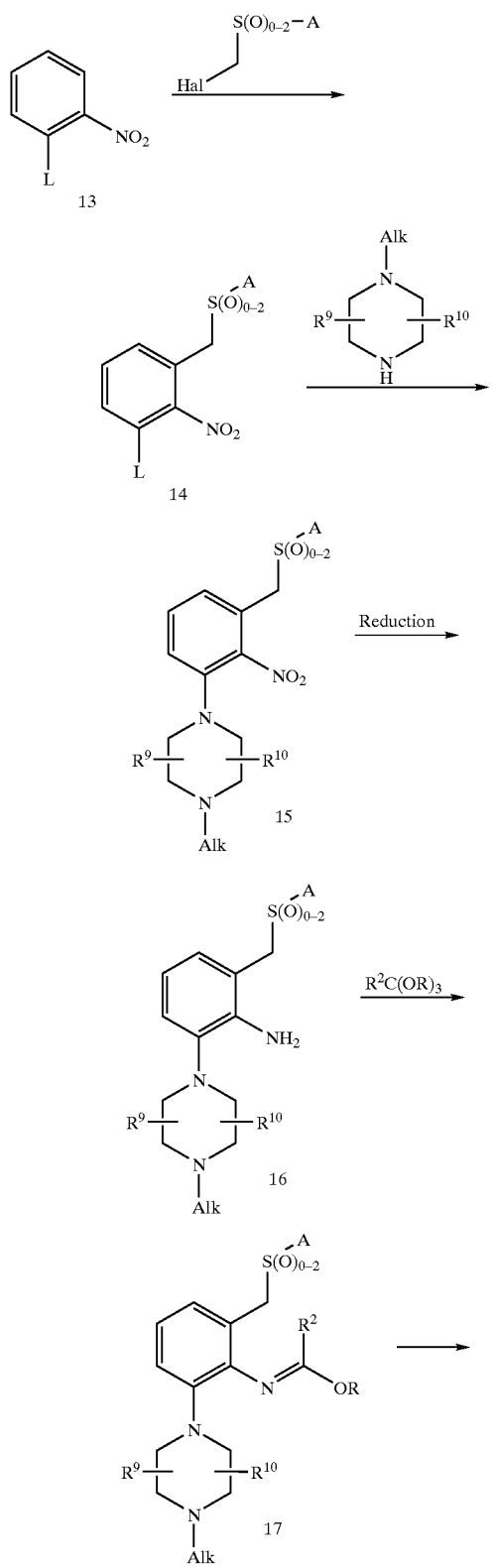

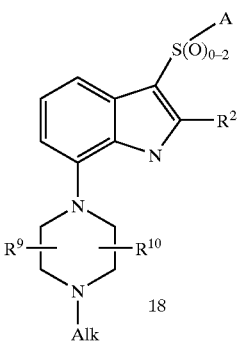

Nitrobenzenes of formula 14 can be prepared from nitrobenzenes of formula 13, with a halomethane derivative such as halomethanesulfonyl benzene, halomethanesulfinyl benzene or halomethanesulfanyl benzene in the presence of a strong base such as potassium tert-butoxide, sodium hydroxyde, lithium hydroxyde, or sodiummethoxide, in a suitable solvent such as THF. Nucleophilic displacement of the nitrobenzene of formula 14 with a leaving group L, such as a halo group, with a 1-alkylpiperazine can afford a nitrobenzene compound of formula 15. Reduction of the nitro group by a variety of methods well known in the art, such as catalytic hydrogenation, preferably in the presence of Pearlman's catalyst (Palladium hydroxyde) in a suitable solvent such as THF can afford an amine of formula 16. Addition of an ortho ester of general formula $R^2C(OR)_3$ wherein R is an alkyl group and $R^2$ is hydrogen or alkyl, in the presence of an acid such p-toluenesulfonic acid, followed by cyclization can afford an indole of formula 18, wherein $R^2$ is hydrogen or alkyl.

GENERAL UTILITY

The compounds of the invention have selective 5-HT6 receptor affinity and as such are expected to be useful in the treatment of certain CNS disorders such as Parkinson's disease, Huntington's disease, anxiety, depression, manic depression, psychosis, epilepsy, obsessive compulsive disorders, migraine, Alzheimer's disease (enhancement of cognitive memory), sleep disorders, feeding disorders such as anorexia and bulimia, panic attacks, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as-hydrocephalus. Such compounds are also expected to be of use in the treatment of certain GI (gastrointestinal) disorders such functional bowel disorder or irritable bowel syndrome (IBS) as well as obesity.

TESTING

The pharmacology of the compounds of this invention was determined by art recognised procedures. The in vitro techniques for determining the affinities of test compounds at the 5-HT6 receptor in radioligand binding and functional assays are described in Example 15.

ADMINISTRATION AND PHARMACEUTICAL COMPOSITION

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1–500 mg daily, preferably 1–100 mg daily, and most preferably 1–30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavours, stabilising, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavours, stabilisers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilising and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilising agents, dispersing agents, suspending agents, thickening agents, or colouring agents. Formulations suitable for topical administration in the mouth include lozenges comprising active agents in a flavoured base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomising spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in Examples 8–14.

EXAMPLES

The following preparations and examples are given to enable those skilled in the art to more clearly understand and to practice the present invention. They should not be considered as limiting the scope of the invention, but merely as being illustrative and representative thereof.

Preparation 1

4-(1H-Indol-7-yl)-piperazine-1-carboxylic acid tert-butyl ester

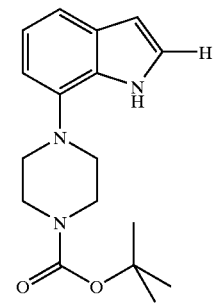

Step 1

Trifluoromethanesulfonic acid 3-methyl-2-nitrophenyl ester

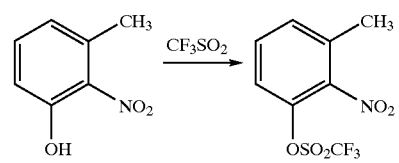

A solution of 3-methyl-2-nitrophenol (15.3 g, 100 mmol) in 200 mL of dichloromethane and 42 mL of triethylamine was cooled to −30° C. and trifluoromethanesulfonic anhydride (21 mL, 125 mmol) was slowly added. After 15 min the mixture was washed with saturated aqueous sodium bicarbonate and brine, dried, and evaporated to a dark oil. Silica gel chromatography (10% ethyl acetate-hexane) afforded 26.7 g of trifluoromethanesulfonic acid 3-methyl-2-nitrophenyl ester as a colorless oil.

Step 2

4-(3-Methyl-2-nitrophenyl)-piperazine-1-carboxylic acid tert-butyl ester

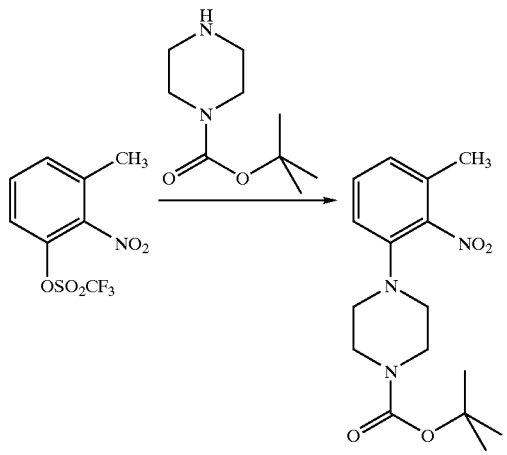

Trifluoromethanesulfonic acid 3-methyl-2-nitrophenyl ester (26.7 g, 93.6 mmol), 1-tert-butoxycarbonyl piperazine (17 g, 91.3 mmol) and triethylamine (14 mL, 100 mmol) in 250 mL of acetonitrile was heated under reflux for 25 h. The mixture was concentrated in vacuo, diluted with water and extracted with ether. The ether was washed with aqueous ammonium hydroxide and brine, dried, and evaporated. Purification by silica gel chromatography (10% ethyl acetate-hexane) afforded 11 g of 4-(3-methyl-2-nitrophenyl)-piperazine-1-carboxylic acid tert-butyl ester as a golden solid, m.p. 101–102° C.

Step 3

4-(1H-Indol-7-yl)-piperazine-1-carboxylic acid tert-butyl ester

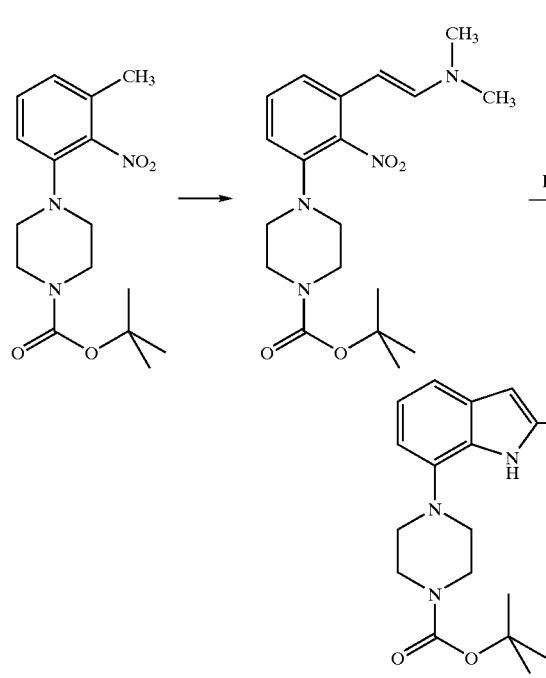

A solution of 4-(3-methyl-2-nitrophenyl)-piperazine-1-carboxylic acid tert-butyl ester (10 g, 31 mmol), N,N-dimethylformamide dimethyl acetal (13.2 mL, 100 mmol) and pyrrolidine (4 mL, 50 mmol) in 45 mL of DMF was heated under reflux for 20 h. The mixture was concentrated in vacuo and the residue was partitioned between ethyl acetate and water. The ethyl acetate was dried and evaporated. The residue was hydrogenated in 200 mL of THF containing 2.5 g of 10% Pd-C at 50 psi for 6 h. The mixture was filtered, concentrated in vacuo, and partitioned between ethyl acetate and aqueous HCl. The ethyl acetate was washed with brine, dried and evaporated. Silica gel chromatography (10% ethyl acetate-hexane) afforded 2.5 g of 4-(1H-Indol-7-yl)-piperazine-1-carboxylic acid tert-butyl ester (19) as a white solid, m.p. 150–151° C.

Preparation 2

4-(1H-indol-5-yl)-piperazine-1-carboxylic acid tert-butyl ester

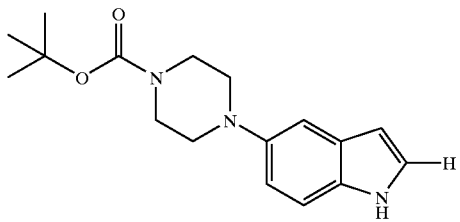

Step 1

4-(3-Methyl-4-nitrophenyl)-piperazine-1-carboxylic acid tert-butyl ester

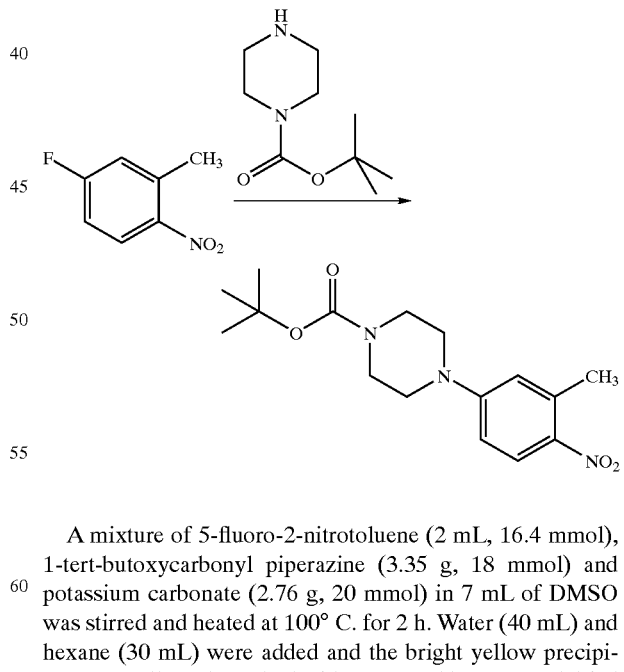

A mixture of 5-fluoro-2-nitrotoluene (2 mL, 16.4 mmol), 1-tert-butoxycarbonyl piperazine (3.35 g, 18 mmol) and potassium carbonate (2.76 g, 20 mmol) in 7 mL of DMSO was stirred and heated at 100° C. for 2 h. Water (40 mL) and hexane (30 mL) were added and the bright yellow precipitate was collected, washed with water and hexane, and dried in vacuo to afford 4.9 g of 4-(3-methyl-4-nitrophenyl)-piperazine-1-carboxylic acid tert-butyl ester, m.p. 145–146° C.

Step 2

4-(1H-Indol-5-yl)-piperazine-1-carboxylic acid tert-butyl ester

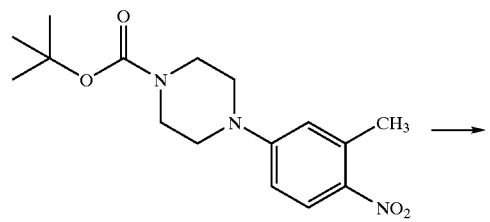

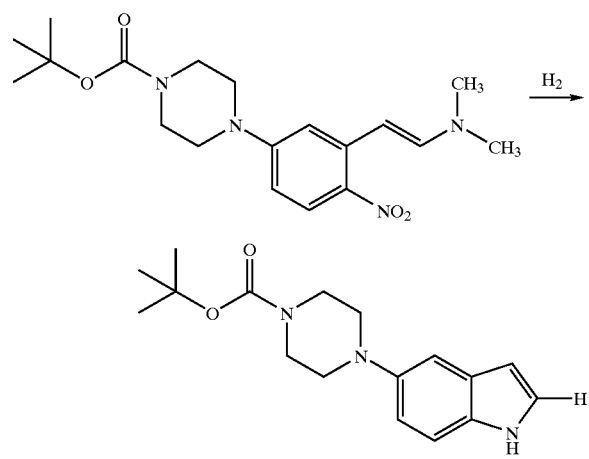

A solution of 4-(3-methyl-4-nitrophenyl)-piperazine-1-carboxylic acid tert-butyl ester (4.3 g, 13.5 mmol), N,N-dimethylformamide dimethyl acetal (2.12 mL, 16 mmol) and pyrrolidine (1.3 mL, 16 mmol) in 15 mL of DMF was heated at 110° C. for 3 h. Additional N,N-dimethylformamide dimethyl acetal (0.7 mL, 5 mmol) and pyrrolidine (0.42 mL, 5 mmol) were added and heating at 110° C. was continued for 15 h. The mixture was concentrated in vacuo, taken into 50 mL of ethanol, and slowly added to a hot (just below boiling) solution of 50 mL of ethanol containing 2 mL of water and 1 g of 10% Pd-C and ammonium formate (4.4 g, 70 mmol). After the addition was complete the mixture was heated under reflux for 10 min. The mixture was filtered, concentrated in vacuo, and partitioned between ether and aqueous sodium carbonate. The ether was washed with water and brine, dried (magnesium sulfate) and evaporated. Silica gel chromatography (20% ethyl acetate-hexane) afforded 3 g of 4-(1H-indol-5-yl)-piperazine-1-carboxylic acid tert-butyl ester (20) as a thick oil.

Alternative Route for the Preparation of 4-(1H-Indol-5-yl)-piperazine-1-carboxylic acid tert-butyl ester (20)

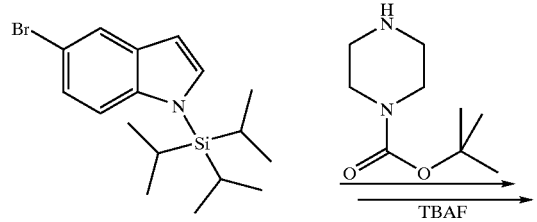

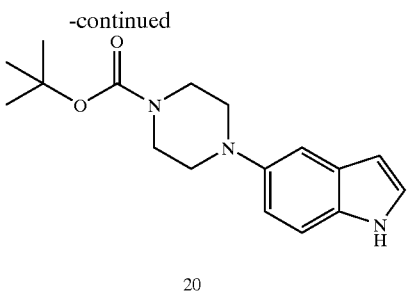

A mixture of 5-bromo-1-triisopropylsilanyl-1H-indole (9 g, 25.5 mmol), 1-tert-butoxycarbonyl piperazine (5 g, 27 mmol), palladium acetate (0.3 g, 1.3 mmol), tri-tert-butyl phosphine (0.263 g, 1.3 mmol) and sodium tert-butoxide (3.65 g, 38 mmol) in 75 mL xylene was heated at 110° for 2 h. The reaction mixture was diluted with 200 mL 50% ethyl ether/hexane and the mixture was filtered through a pad of silica gel. Enough 10% ethyl acetate/hexane was used to elute 4-(1-triisopropylsilanyl-1H-indol-5-yl)-piperazine-1-carboxylic acid tert-butyl ester (11.7 g) which was recovered as a light brown heavy syrup by concentrating the eluate under reduced pressure.

To a solution of 4-(1-triisopropylsilanyl-1H-indol-5-yl)-piperazine-1-carboxylic acid tert-butyl ester (11.7 g, 25 mmol) in 150 mL THF was added 26 mL 1.0 M tetrabutylammonium fluoride in THF. After 2 h at room temperature, the solution was concentrated under reduced pressure and the residue was partitioned between 100 mL ethyl ether and 20 mL saturated sodium bicarbonate. The organic phase was washed with 20 mL water, 10 mL saturated sodium chloride, dried (magnesium sulfate) and concentrated under reduced pressure. The residue was subjected to column chromatography over silica gel eluting with 20% ethyl acetate/hexane affording 7 g 4-(1H-indol-5-yl)-piperazine-1-carboxylic acid tert-butyl ester (20).

Preparation 3

4-(2-Methyl-1H-indol-7-yl)-piperazine-1-carboxylic acid tert-butyl ester

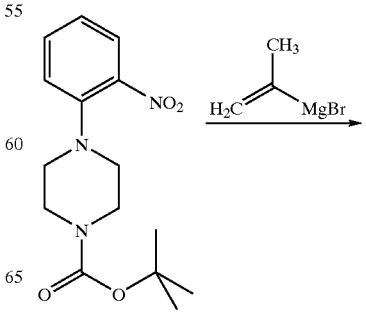

-continued

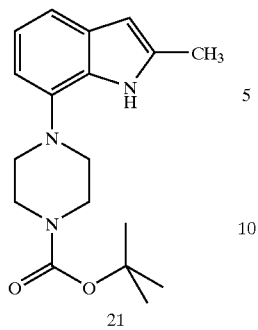

21

Isopropenyl magnesium bromide (234 mL of a 0.5 M solution in THF, 117 mmol) was slowly added to a −40° C. solution of 4-(4-nitrophenyl)-piperazine-1-carboxylic acid tert-butyl ester (12 g, 39 mmol) in 200 mL of THF and the resulting mixture was stirred at −40° C. for 20 min. Saturated aqueous ammonium chloride was added and the mixture was extracted with ethyl acetate. The extract was washed with water and brine, dried (sodium sulfate) and evaporated. Silica gel chromatography (20% ethyl acetate-hexane) afforded 4.8 g of 4-(2-methyl-1H-indol-7-yl)-piperazine-1-carboxylic acid tert-butyl ester (21) as an oil, mass spec, M+ 315.

Preparation 4

4-(1H-Indol-7-yl)-piperidine-1-carboxylic acid tert-butyl ester

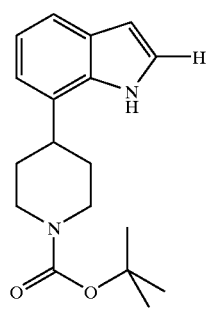

Step 1

4-Hydroxy-4-(1H-indol-7-yl)-piperidine-1-carboxylic acid tert-butyl ester

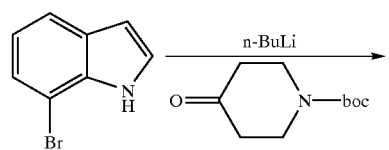

-continued

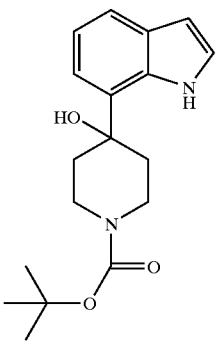

To a solution of 7-bromoindole (400 mg, 2.04 mmol) in THF (20 mL) under an argon atmosphere and cooled to −78° C. was added n-butyllithium (3.1 mL, 2.0M, 6.1 mmol) dropwise. The reaction was stirred at −78° C. for 15 minutes then warmed to 5° C. and maintained for 30 minutes. The reaction was cooled back to −78° C. and 4-oxo-piperidine-1-carboxylic acid tert-butyl ester (813 mg, 4.08 mmol) was added dropwise in THF (5 mL). The reaction was allowed to come to room temperature and stirred for 1 h. The reaction was quenched with water (15 mL) and extracted with EtOAc (3×20 mL). The combined acetate layers were washed with brine, dried over MgSO$_4$ and filtered. The filtrate was concentrated in vacuo and chromatographed on silica eluting with 20% acetone in hexanes to afford 4-hydroxy-4-(1H-indol-7-yl)-piperidine-1-carboxylic acid tert-butyl ester as a white foam (520 mg).

Step 2

4-(1H-Indol-7-yl)-3,6-dihydro-2H-pyridine-1-carboxylic acid tert-butyl ester

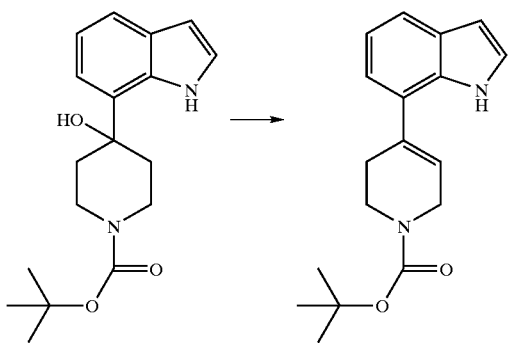

To a solution of 4-hydroxy-4-(1H-indol-7-yl)-piperidine-1-carboxylic acid tert-butyl ester (117 mg, 0.37 mmol) in pyridine (5 mL) was added POCl$_3$ (70 μL, 0.74 mmol) in a single portion. The reaction was stirred for 24 h, quenched with the slow addition of water (10 mL) and extracted with EtOAc (3×10 mL). The combined acetate layers were washed with brine, dried (MgSO$_4$) and concentrated to afford 4-(1H-indol-7-yl)-3,6-dihydro-2H-pyridine-1-carboxylic acid tert-butyl ester as a light yellow oil (100 mg).

Step 3

4-(1H-Indol-7-yl)-piperidine-1-carboxylic acid tert-butyl ester

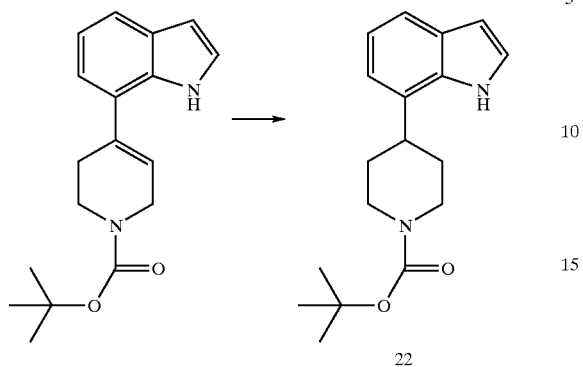

To a solution of 4-(1H-indol-7-yl)-3,6-dihydro-2H-pyridine-1-carboxylic acid tert-butyl ester (100 mg) in EtOH (20 mL) was added 10% Pd/C (20 mg). The reaction was placed on a Parr shaker at 55 psi H₂ for 24 h. The reaction was filtered through Celite™ and concentrated to afford 4-(1H-indol-7-yl)-piperidine-1-carboxylic acid tert-butyl ester (22) as a clear oil (78 mg).

Example 1

3-Benzenesulfonyl-7-piperazin-1-yl-1H-indole

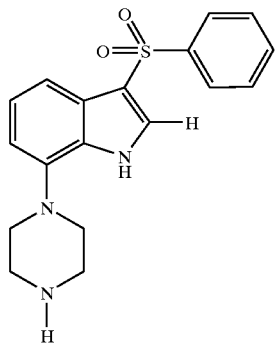

Step 1

4-(3-Phenylsulfanyl-1H-indol-7-yl)-piperazine-1-carboxylic acid tert-butyl ester

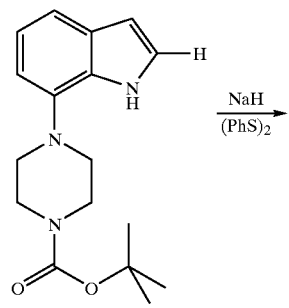

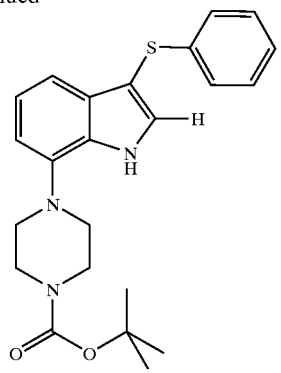

Sodium hydride (0.4 g of 60% dispersion in mineral oil, 10 mmol) was added to an ice-cooled solution of 4-(1H-Indol-7-yl)-piperazine-1-carboxylic acid tert-butyl ester (19) prepared as described in Preparation 1 (2.3 g, 7.6 mmol) in 20 mL DMF and the resulting mixture was stirred for 10 min. Phenyl disulfide (1.85 g, 8.5 mmol) was added and the solution was stirred at room temperature for 16 h. Water was added and the mixture was extracted with ethyl acetate. The extract was washed with brine, dried and evaporated to afford 2.9 g of 4-(3-phenylsulfanyl-1H-indol-7-yl)-piperazine-1-carboxylic acid tert-butyl ester) as a white solid, m.p. 165–166° C.

Step 2

4-(3-Benzenesulfonyl-1H-indol-7-yl)-piperazine-1-carboxylic acid tert-butyl ester

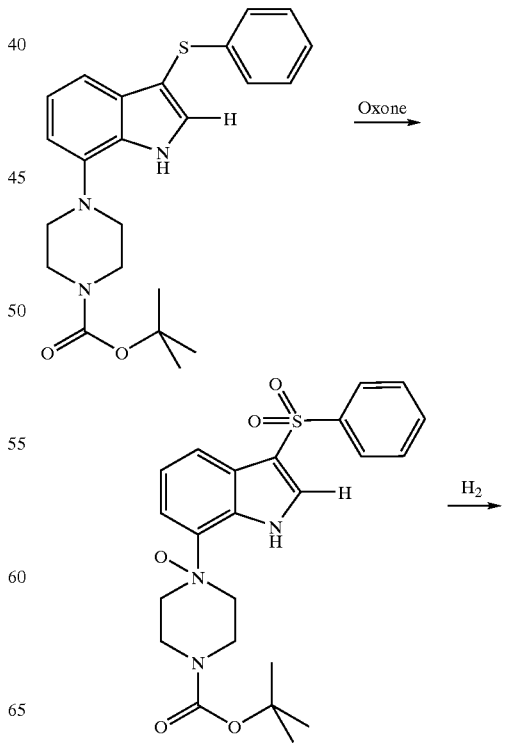

-continued

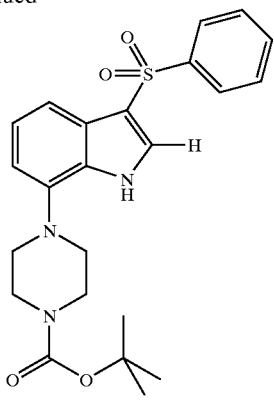

Oxone™ (9.2 g, 15 mmol) in 40 mL of water was added to a stirred solution of 4-(3-phenylsulfanyl-1H-indol-7-yl)-piperazine-1-carboxylic acid tert-butyl ester(2.9 g ) in 50 mL of methanol and 10 mL of THF. The mixture was stirred for 2 h, diluted with water, and extracted with ethyl acetate. The ethyl acetate was dried (sodium sulfate) and evaporated to afford a solid residue of the sulfone N-oxide. This was dissolved in 50 mL of methanol and hydrogenated at atmospheric pressure over 0.3 g of 10% Pd-C for 12 h. Dichloromethane was added and the mixture was filtered and evaporated. Trituration of the residue with ether afforded 2.2 g of 4-(3-benzenesulfonyl-1H-indol-7-yl)-piperazine-1-carboxylic acid tert-butyl ester as a white solid, m.p. 168–169° C.

Step 3

3-Benzenesulfonyl-7-piperazin-1-yl-1H-indole hydrochloride

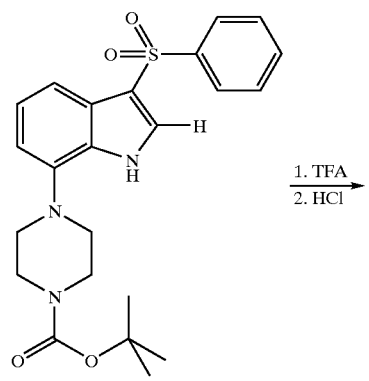 1. TFA
2. HCl

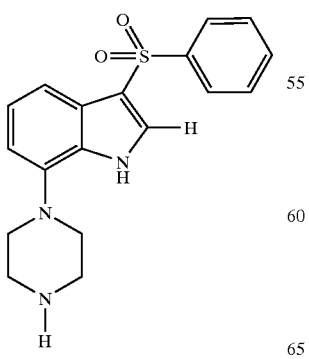

4-(3-Benzenesulfonyl-1H-indol-7-yl)-piperazine-1-carboxylic acid tert-butyl ester (1 g, 2.2 mmol) was dissolved in 5 mL of dichloromethane and 6 mL of trifluoroacetic acid was added. After 10 min the mixture was concentrated in vacuo, taken into water, and washed with ether. The aqueous layer was basified with ammonium hydroxide, extracted with dichloromethane, and the extract was dried (sodium sulfate) and evaporated to afford the crude free base. The hydrochloride salt was crystallized from ethanol to afford 550 mg of 3-benzenesulfonyl-7-piperazin-1-yl-1H-indole hydrochloride (101), m.p. 278–280° C.

Similarly replacing in Step 1 phenyl disulfide with the appropriate substituted phenyl disulfides, the following compounds were prepared:

7-piperazin-1-yl-3-(toluene-4-sulfonyl)-1H-indole (102), m.p. 285–287° C.;
3-(3,4-dichloro-benzenesulfonyl)-7-piperazin-1-yl-1H-indole (103), m.p. 290° C.;
3-(4-fluoro-benzenesulfonyl)-7-piperazin-1-yl-1H-indole (104), m.p. 247–249° C.;
3-(3,5-dichloro-benzenesulfonyl)-7-piperazin-1-yl-1H-indole (105), m.p. 290° C.;
3-(2,4-dichloro-benzenesulfonyl)-7-piperazin-1-yl-1H-indole (106), m.p. 300° C.;
3-(3-chloro-benzenesulfonyl)-7-piperazin-1-yl-1H-indole (107), m.p. 295° C.;
3-(2-chloro-benzenesulfonyl)-7-piperazin-1-yl-1H-indole (108), m.p. 280–282° C.;
7-piperazin-1-yl-3-(2-trifluoromethyl-benzenesulfonyl)-1H-indole (109), m.p. 186–187°
3-(3-chloro-benzenesulfonyl)-5-piperazin-1-yl-1H-indole (110), m.p. 192–197° C.; and
3-(3,4-dichloro-benzenesulfonyl)-5-piperazin-1-yl-1H-indole (111), m.p. >300° C.

Similarly replacing in Step 1 phenyldisulfide with the appropriate heteroaryl disulfides the following compounds were prepared:
7-piperazin-1-yl-3-(pyridine-4-sulfonyl)-1H-indole (112), m.p. 207–208° C.;
7-piperazin-1-yl-3-(pyridine-2-sulfonyl)-1H-indole (113), m.p. 198–199° C.;
2-(7-piperazin-1-yl-1H-indole-3-sulfonyl)-benzothiazole (114), m.p. 295° C.; and
6-piperazin-1-yl-3-(pyridine-2-sulfonyl)-1H-indole (115) m.p. 246.7–247.2° C.

Example 2

3-Benzenesulfonyl-5-piperazin-1-yl-1H-indole

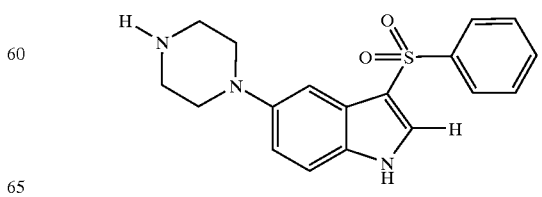

Step 1

4-(3-Phenylsulfanyl-1H-indol-5-yl)-piperazine-1-carboxylic acid tert-butyl ester

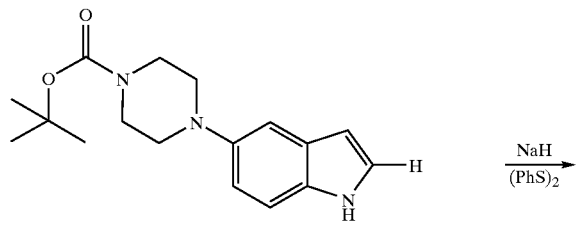

NaH
(PhS)₂
→

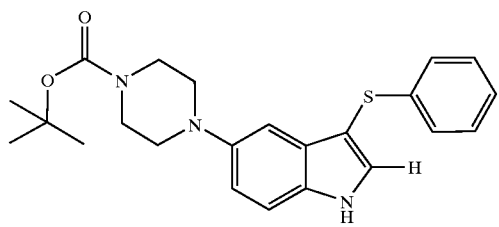

Sodium hydride (0.29 g, 12 mmol) was added to an ice-cooled solution of 4-(1H-Indol-5-yl)-piperazine-1-carboxylic acid tert-butyl ester (20) prepared as described in Preparation 2 (3 g, 10 mmol) in 30 mL DMF and the resulting mixture was stirred for 10 min. Phenyl disulfide (2.6 g, 12 mmol) was added and the solution was stirred at room temperature for 16 h. Water was added and the mixture was extracted with ethyl ether. The extract was washed with brine, dried and evaporated to afford 3.83 g of 4-(3-phenylsulfanyl-1H-indol-5-yl)-piperazine-1-carboxylic acid tert-butyl ester) as a tan crystalline solid, m.p. 174° C.

Step 2

4-(3-Benzenesulfonyl-1H-indol-5-yl)-piperazine-1-carboxylic acid tert-butyl ester

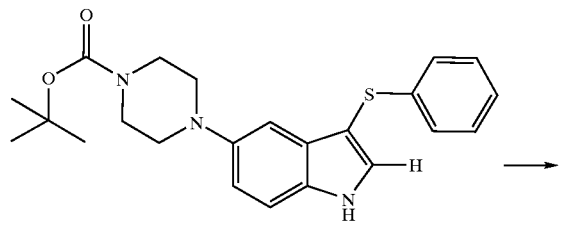

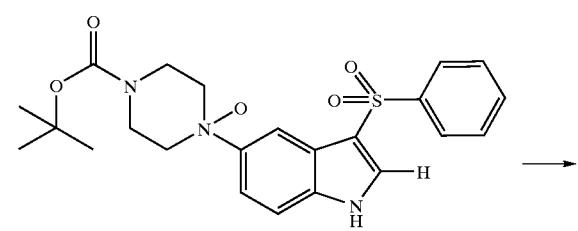

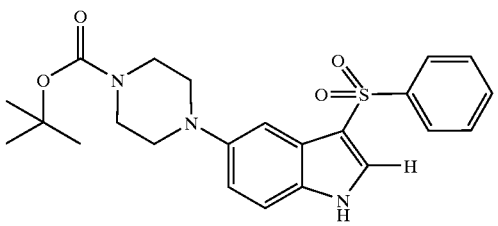

A solution of 4-(3-phenylsulfanyl-1H-indol-5-yl)-piperazine-1-carboxylic acid tert-butyl ester (2.57 g, 6.28 mmol) in dichloromethane (50 mL) was cooled in ice and treated with 70% m-chloroperbenzoic acid (4.5 g). The cooling bath was removed and stirring at room temperature continued for 3 h. The mixture was then concentrated to dryness, the residue treated with ethyl ether (50 mL), stirred well for 10 min, filtered, the filter cake washed well with ethyl ether and air-dried to give the sulfone N-oxide m-chlorobenzoic acid salt as a beige solid. This was dissolved in 45 mL of DMF, treated with 0.24 g of Pearlmann's catalyst, and hydrogenated at atmospheric pressure for 4 h. The mixture was then filtered free of catalyst, the filtrate concentrated to dryness, the residue taken up in 450 mL ethyl acetate-chloroform (4:1), washed with 1.5 M sodium carbonate and then water, dried, filtered, and partially concentrated to ~50 mL. After the mixture was diluted with 75 mL of ethyl ether, the solid was filtered, washed with ethyl ether and dried affording 2.4 g of 4-(3-benzenesulfonyl-1H-indol-5-yl)-piperazine-1-carboxylic acid tert-butyl ester as a pinkish-beige solid, m.p. 238–41° C. (dec.).

Step 3

3-Benzenesulfonyl-5-piperazin-1-yl-1H-indole hydrochloride

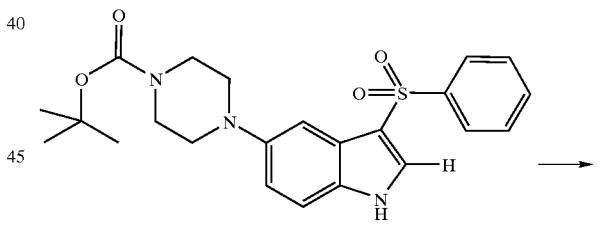

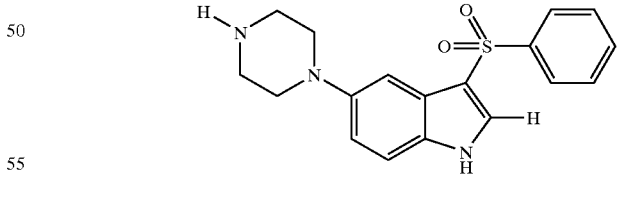

4-(3-Benzenesulfonyl-1H-indol-5-yl)-piperazine-1-carboxylic acid tert-butyl ester (0.5 g, 1.13 mmol) was dissolved in 5 mL of ethanol and 3 mL of conc. hydrochloric acid were added. The mixture was heated to a gentle boil for 2–3 min, cooled to room temperature, basified with ammonium hydroxide, and diluted with 20 mL of water. After the mixture was allowed to stand overnight, the solid was filtered, washed with water and dried to give 0.37 g of 3-benzenesulfonyl-5-piperazin-1-yl-1H-indole (201) as a tan crystalline solid, m.p. 254–264° C. (dec).

Similarly, following the procedure described above, but replacing phenyl disulfide with the appropriate substituted phenyl disulfides, the following compounds were prepared:

3-(2,3-dichloro-benzenesulfonyl)-5-piperazin-1-yl-1H-indole (202), m.p. >300° C.;
5-piperazin-1-yl-3-(4-trifluoromethyl-benzenesulfonyl)-1H-indole (203), m.p. 274.9–280.9° C.;
3-(4-chloro-benzenesulfonyl)-5-piperazin-1-yl-1H-indole (204), m.p. 282–286.4° C.;
3-(3,5-dichloro-benzenesulfonyl)-5-piperazin-1-yl-1H-indole (205), m.p. >300° C.;
3-(2-chloro-benzenesulfonyl)-5-piperazin-1-yl-1H-indole (206), m.p. >300° C.;
3-(4-fluoro-benzenesulfonyl)-5-piperazin-1-yl-1H-indole (207), m.p. 289–291° C.; and
3-(3-Chloro-benzenesulfonyl)-7-piperidin-4-yl-1H-indole (208), m.p. 272.3–272.9° C.

Example 3

3-Benzenesulfonyl-7-piperidin-4-yl-1H-indole

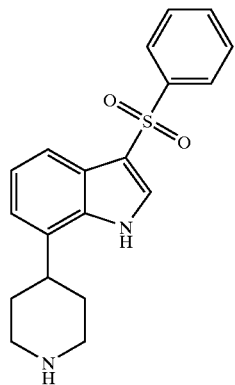

Step 1

4-(3-Phenylsulfanyl-1H-indol-7-yl)-piperidine-1-carboxylic acid tert-butyl ester

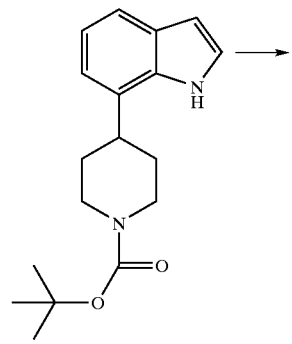

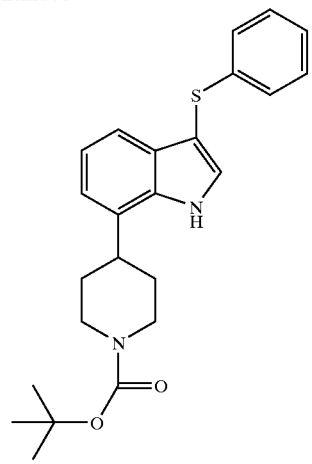

To a solution of 4-(1H-indol-7-yl)-piperidine-1-carboxylic acid tert-butyl ester (22) prepared as described herein in Preparation 4 (220 mg, 0.73 mmol) in DMF (15 mL) was added NaH (95%, 25 mg, 0.95 mmol) in a single portion. The reaction was stirred at room temperature for 30 minutes and phenyldisulfide (185 mg, 0.88 mmol) was added. The reaction was stirred at room temperature for 24 h and poured into water (50 mL). The aqueous layer was extracted with EtOAc (3×20 mL) and the combined organic layers were washed with brine, dried (MgSO$_4$) and concentrated in-vacuo. Flash chromatography eluting with 20% acetone in hexanes afforded 4-(3-phenylsulfanyl-1H-indol-7-yl)-piperidine-1-carboxylic acid tert-butyl ester as a tan solid (200 mg).

Step 2

4-(3-Benzenesulfonyl-1H-indol-7-yl)-piperidine-1-carboxylic acid tert-butyl ester

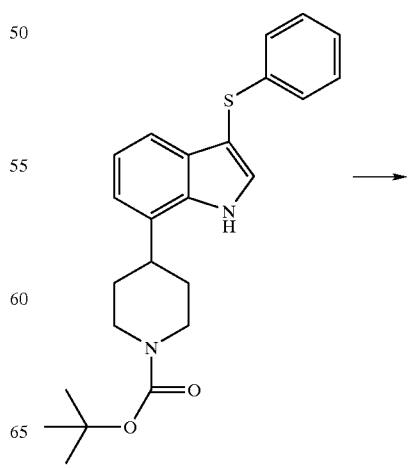

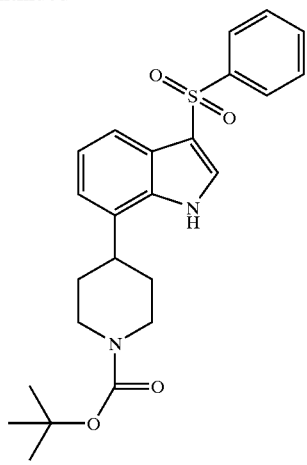

To an ice cold solution of 4-(3-phenylsulfanyl-1H-indol-7-yl)-piperidine-1-carboxylic acid tert-butyl ester (190 mg, 0.48 mmol) in methylene chloride (20 mL) under a nitrogen atmosphere was added m-chloroperbenzoic acid (166 mg, 0.96 mmol) portionwise. The reaction, complete after 2 h at 0° C., was diluted with methylene chloride (30 mL) and washed with water (15 ml). The organic phase was washed with 5% KOH (15 mL) and concentrated to afford 4-(3-benzenesulfonyl-1H-indol-7-yl)-piperidine-1-carboxylic acid tert-butyl ester (156 mg).

Step 3
3-Benzenesulfonyl-7-piperidin-4-yl-1H-indole

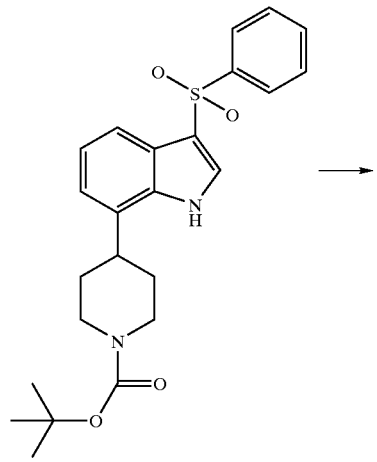

To a solution of 4-(3-benzenesulfonyl-1H-indol-7-yl)-piperidine-1-carboxylic acid tert-butyl ester (200 mg, 0.45 mmol) in methylene chloride (20 mL) under a nitrogen atmosphere was added TFA (5 mL). After 30 minutes the reaction was concentrated in vacuo and partitioned between 10% aq. KOH (30 mL) and EtOAc (30 mL). The acetate layer was dried ($MgSO_4$) and concentrated to afford the product as a light brown oil. Trituration with ether afforded 3-benzenesulfonyl-7-piperidin-4-yl-1H-indole (301) as a tan solid (113 mg) m.p. 186–189.5° C.

Example 4

3-Benzenesulfonyl-1-methyl-7-piperazin-1-yl-1H-indole

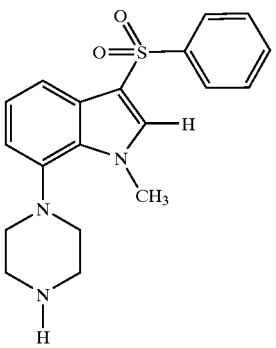

Step 1
4-(3-Benzenesulfonyl-1-methyl-1H-indol-7-yl)-piperazine-1-carboxylic acid tert-butyl ester

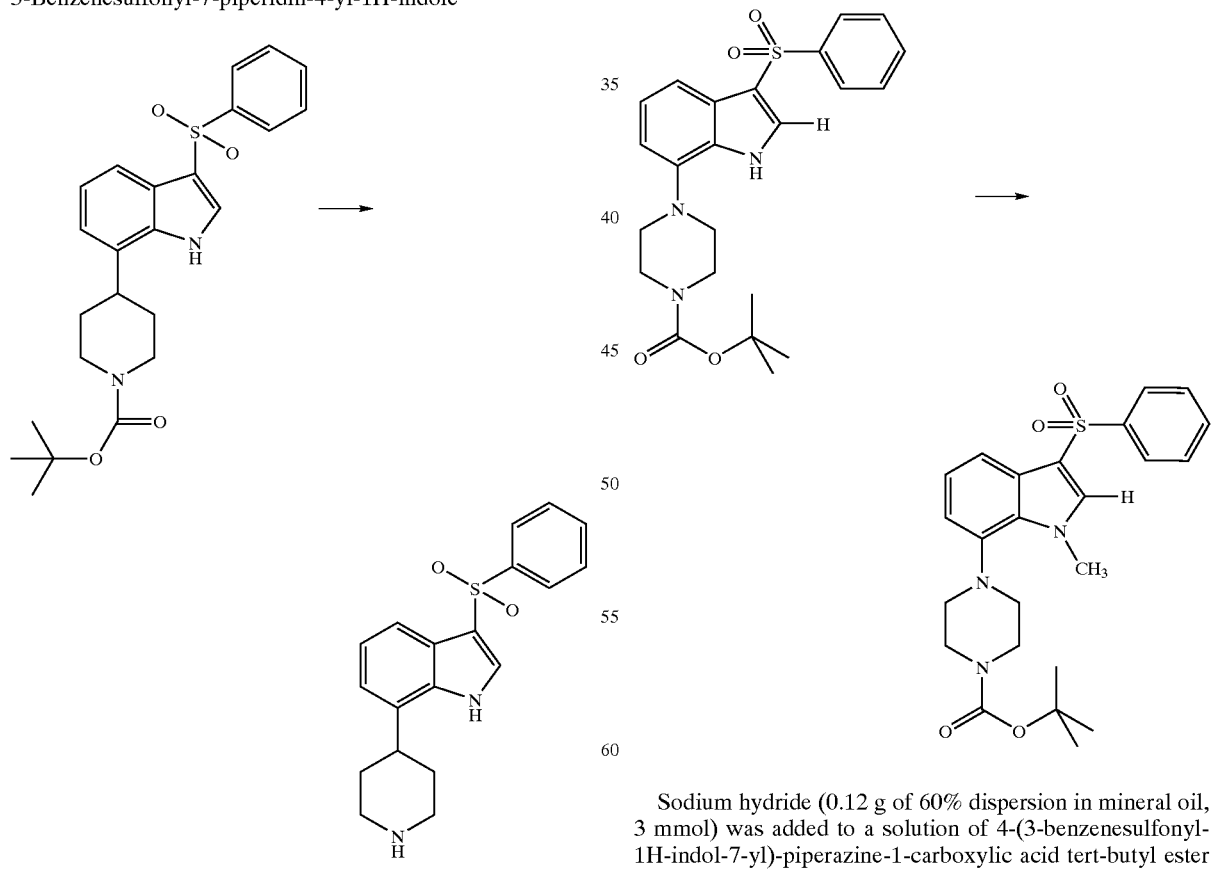

Sodium hydride (0.12 g of 60% dispersion in mineral oil, 3 mmol) was added to a solution of 4-(3-benzenesulfonyl-1H-indol-7-yl)-piperazine-1-carboxylic acid tert-butyl ester (1 g, 2.3 mmol) in 20 mL of DMF with ice cooling. After stirring 15 min at room temperature the mixture was treated with methyl iodide (0.17 mL, 3 mmol). Water was added and the mixture was extracted with ethyl acetate. The extract was washed with water and brine, dried (sodium sulfate) and evaporated. Silica gel chromatography (20% ethyl acetate-hexane) afforded 0.9 g of 4-(3-benzenesulfonyl-1-methyl-1H-indol-7-yl)-piperazine-1-carboxylic acid tert-butyl ester as a foam, mass spec. M+ 455.

Step 2
3-Benzenesulfonyl-1-methyl-7-piperazin-1-yl-1H-indole

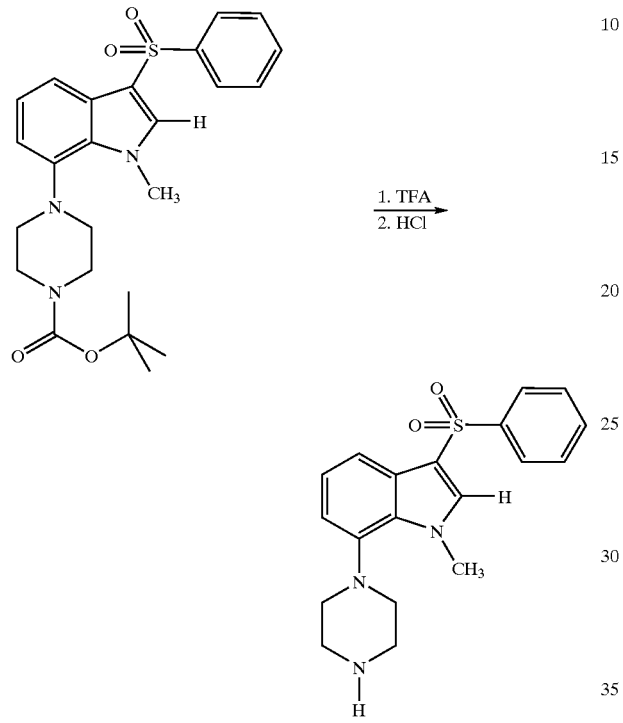

Deprotection of 4-(3-benzenesulfonyl-1-methyl-1H-indol-7-yl)-piperazine-1-carboxylic acid tert-butyl ester as described in step 3 Example 1 afforded the free base of 3-benzenesulfonyl-1-methyl-7-piperazin-1-yl-1H-indole hydrochloride (401) as a white solid, m.p. 249–250° C. The hydrochloride salt had m.p. 293–295° C.

Similarly following the procedure described above but replacing 4-(3-benzenesulfonyl-1H-indol-7-yl)-piperazine-1-carboxylic acid tert-butyl ester in Step 1 with the appropriate indole derivatives the following compounds were prepared:

1-methyl-7-piperazin-1-yl-3-(pyridine-2-sulfonyl)-1H-indole (402), m.p. 297–298°
3-benzenesulfonyl-1-methyl-5-piperazin-1-yl-1H-indole (403), m.p. 239–240° C. (dec);
1-methyl-7-piperazin-1-yl-3-(2-trifluoromethyl-benzenesulfonyl)-1H-indole (404), m.p. 295° C.;
3-(4-fluoro-benzenesulfonyl)-1-methyl-7-piperazin-1-yl-1H-indole (405), m.p. 300° C.;
1-methyl-7-piperazin-1-yl-3-(3-trifluoromethyl-benzenesulfonyl)-1H-indole (406), m.p. 279–280° C.;
3-(2-chloro-benzenesulfonyl)-1-methyl-7-piperazin-1-yl-1H-indole (407), m.p. 295–297° C.;
3-(3-chloro-benzenesulfonyl)-1-methyl-7-piperazin-1-yl-1H-indole (408), m.p. 300° C.;
3-(2,3-dichloro-benzenesulfonyl)-1-methyl-5-piperazin-1-yl-1H-indole (409), m.p. 198–203° C.;
1-methyl-5-piperazin-1-yl-3-(3-trifluoromethyl-benzenesulfonyl)-1H-indole (410), m.p. 235–240° C.;
3-(3,5-dichloro-benzenesulfonyl)-1-methyl-5-piperazin-1-yl-1H-indole (411), m.p. 282–284.5° C.;
1-methyl-7-piperazin-1-yl-3-(pyridine-2-sulfonyl)-1H-indole (412), m.p. 297–298°
3-(4-fluoro-benzenesulfonyl)-1-methyl-5-piperazin-1-yl-1H-indole (413), m.p. 195–207° C.;
3-(2-chloro-benzenesulfonyl)-1-methyl-5-piperazin-1-yl-1H-indole (414), m.p. 249.6–253° C.;
3-(3-chloro-benzenesulfonyl)-1-methyl-5-piperazin-1-yl-1H-indole (415), m.p. 185.5–188.5° C.; and
1-methyl-5-piperazin-1-yl-3-(pyridine-2-sulfonyl)-1H-indole (416), m.p. 256.8–257.5° C.;

Similarly following the procedure described above but replacing in Step 1 methyl iodide with isopropyl iodide the following compound was prepared:

3-benzenesulfonyl-1-isopropyl-5-piperazin-1-yl-1H-indole (417) M+H=384.

Example 5

3-Benzenesulfonyl-7-(4-methyl-piperazin-1-yl)-1H-indole

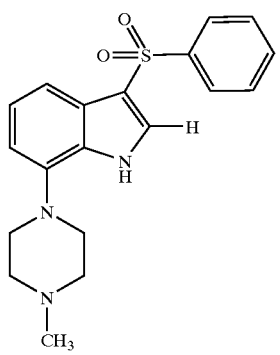

A solution of 3-benzenesulfonyl-7-piperazin-1-yl-1H-indole (101) (500 mg, 1.46 mmol) and 1 mL of 37% aqueous formaldehyde in 25 mL of ethanol was hydrogenated at atmospheric pressure in the presence of 250 mg of 10% Pd-C for 30 min. The mixture was filtered, diluted with water and extracted with ethyl acetate. The ethyl acetate was washed with water and brine, dried, and evaporated to yield the crude free base of 3-benzenesulfonyl-7-(4-methyl-piperazin-1-yl)-1H-indole. The hydrochloride salt was crystallized from ethanol-ether to afford 290 mg of (501), m.p. 160–162° C.

Similarly following the procedure described above but replacing 3-benzenesulfonyl-7-piperazin-1-yl-1H-indole with the appropriate indoles, the following compounds were prepared:

3-benzenesulfonyl-1-methyl-7-(4-methyl-piperazin-1-yl)-1H-indole (502), m.p. 260–262° C.;
3-(3,4-dichloro-benzenesulfonyl)-7-(4-methyl-piperazin-1-yl)-1H-indole (503), m.p. 196–203° C.;
3-(2-chloro-benzenesulfonyl)-7-(4-methyl-piperazin-1-yl)-1H-indole (504), m.p. 168.5–175.9° C.;
3-(3-chloro-benzenesulfonyl)-7-(4-methyl-piperazin-1-yl)-1H-indole (505), m.p. 163–171° C.;
3-(2,4-dichloro-benzenesulfonyl)-7-(4-methyl-piperazin-1-yl)-1H-indole (506), m.p. 199–203° C.;
3-(3,5-dichloro-benzenesulfonyl)-7-(4-methyl-piperazin-1-yl)-1H-indole (507), m.p. 237.1–241.5° C.;

7-(4-methyl-piperazin-1-yl)-3-(2-trifluoromethyl-benzenesulfonyl)-1H-indole (508), m.p. 237.1–241.5° C.;

3-benzenesulfonyl-5-(4-methyl-piperazin-1-yl)-1H-indole (509) M+H=356; and 3-(4-fluoro-benzenesulfonyl)-7-(1-methyl-piperidin-4-yl)-1H-indole (510), m.p. 178–182° C.

Similarly following the procedure described above but replacing formaldehyde with the appropriate aldehydes, the following compounds were prepared:

3-benzenesulfonyl-7-(4-cyclopropylmethyl-piperazin-1-yl)-1H-indole (511), m.p. 280–282° C.;

3-benzenesulfonyl-7-(4-propyl-piperazin-1-yl)-1H-indole (512), m.p. 290–295° C., and 3-benzenesulfonyl-7-(4-ethyl-piperazin-1-yl)-1H-indole (513), m.p. 274–275° C.

Alterative preparation of 3-benzenesulfonyl-7-(4-methyl-piperazin-1-yl)-1H-indole (501)

Step 1

1-Benzenesulfonylmethyl-3-chloro-2-nitro-benzene

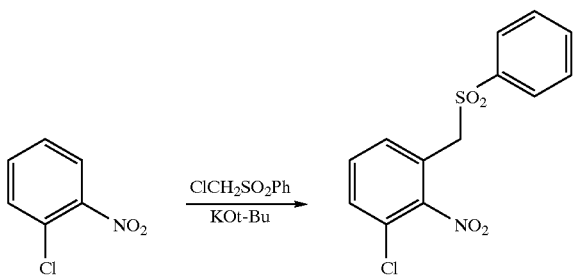

100 g 1-Chloro-2-nitro-benzene (0.52 mole) were dissolved in 450 mL THF containing 86 g chloromethanesulfonyl-benzene (0.52 mole). They were charged into a 12% (1M) solution of potassieum tert-butoxide (KotBu) in THF (1.1 kg, 2.2 eq) which was chilled to −48° C. and mechanically stirred. The rate of addition was controlled such that the internal temperature of the THF/KOtBu solution did not exceed −40° C. Following the addition, the mixture (deep purple) was stirred for another 3 hours at −45° C. to −40° C. until TLC analysis, 4:1 hexanes:ethylacetate showed all starting material had been consumed. The mixture was quenched with 200 mL acetic acid and warmed from this quench to −15° C. This was then slowly quenched with a total 2.4L water,. The mixture stirred for an additional 18 hours, and was filtered and washed with 1.5L water in 500 mL aliquots. The cake was washed with hexanes and vacuum-oven dried at 45–50° C. under nitrogen purge to yield 136 g. of 1-benzenesulfonylmethyl-3-chloro-2-nitro-benzene, mp 141–142° C.

Step 2

1-(3-Benzenesulfonylmethyl-2-nitro-phenyl)-4-methyl-piperazine

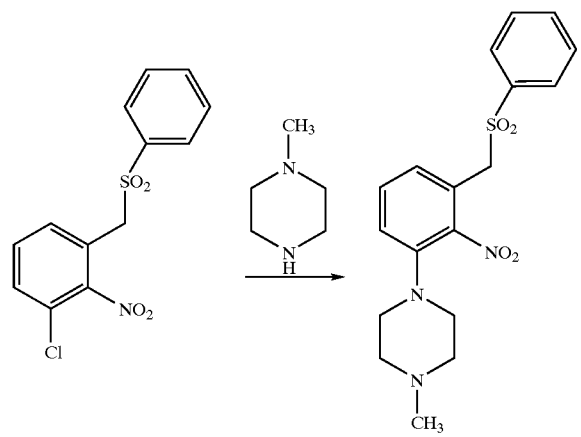

10 g of 1-benzenesulfonylmethyl-3-chloro-2-nitro-benzene were slurried in 25 mL N-methylpiperazine under nitrogen and stirred. The mixture was heated to 80° C. (oil bath temperature) for a period of 14 hours. The reaction was quenched at 80° C. with 125 mL water, and the thick slurry was filtered, washed with 100 mL water and 100 mL hexanes., and vacuum dried at 45° C. under nitrogen purge for 4 hours, to yield 11.7 g of 1-(3-benzenesulfonylmethyl-2-nitro-phenyl)-4-methyl-piperazine mp 180–182° C.

Step 3

2-Benzenesulfonylmethyl-6-(4-methyl-piperazin-1-yl)-phenylamine

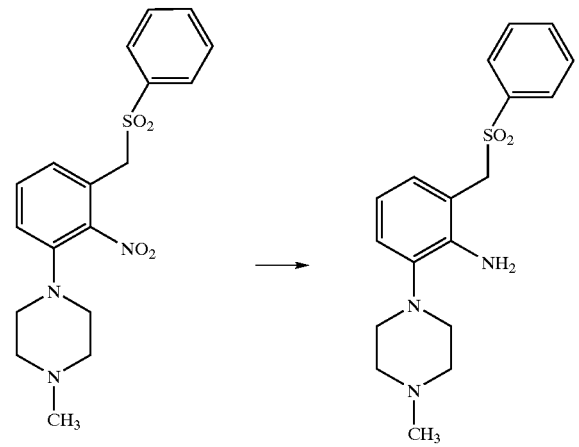

A solution of 1-(3-benzenesulfonylmethyl-2-nitro-phenyl)-4-methyl-piperazine (25 g) in tetrahydrofuran (500 mL) prepared by heating to 45° C. was added to a pre-hydrogenated suspension of Pearlman's catalyst (20% Pd(OH)$_2$/C; 0.5 g) in tetrahydrofuran (20 mL). Stirring is continued under a hydrogen atmosphere at 45° C. until the reaction is complete (ca. 29 hours). After cooling, the catalyst is filtered off on Solkafloc™ (10 g) and washed with tetrahydrofuran (50 mL). The filtrate is concentrated under vacuum to give 24.9 g of 2-benzenesulfonylmethyl-6-(4-methyl-piperazin-1-yl)-phenylamine as a foam.

Step 4

3-benzenesulfonyl-7-(4-methyl-piperazin-1-yl)-1H-indole

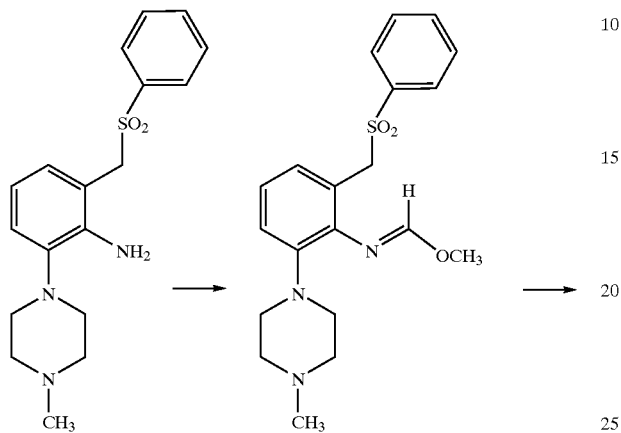

To a solution of 2.3 g of 2-benzenesulfonylmethyl-6-(4-methyl-piperazin-1-yl)-phenylamine in 20 mL trimethyl orthoformate was added p-toluenesulfonic acid (120 mg). The mixture was heated under reflux in a nitrogen atmosphere for 2 hours. The mixture was cooled to 60° C. and one flake of KOH was added. The mixture was reheated to reflux for 1.5 hours. The heating oil bath was turned off and the mixture stirred overnight under nitrogen. The mixture was treated with 50 mL saturated ammonium chloride solution and 100 mL EtOAc. The purple organic layer was separated from the clear aqueous solution, and washed with water (45 mL) and evaporated to a foam. This foam was dissolved in 80 mL 200 proof EtOH. After dissolution, the freebase crystallized. This mixture was heated under reflux to redissolve the solid, and after removal of the heating, 5 mL of a saturated solution of HCl in ethanol was added to this mixture. The mixture was cooled with stirring to room temperature and seeded to ensue immediate crystallization. The mixture was concentrated to ca. 40 mL and filtered. This collected solid was washed with ca. 3 mL EtOH and vacuum oven dried at 50° C. to give 1.9 g 3-benzenesulfonyl-7-(4-methyl-piperazin-1-yl)-1H-indole (501) mp 160–162° C.

Example 6

3-Benzenesulfonyl-2-methyl-7-piperazin-1-yl-1H-indole

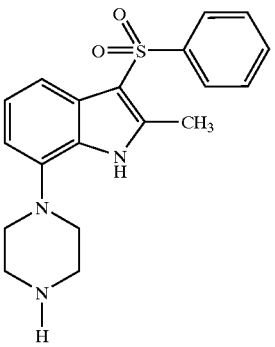

Step 1

4-(2-Methyl-3-phenylsulfanyl-1H-indol-7-yl)-piperazine-1-carboxylic acid tert-butyl ester

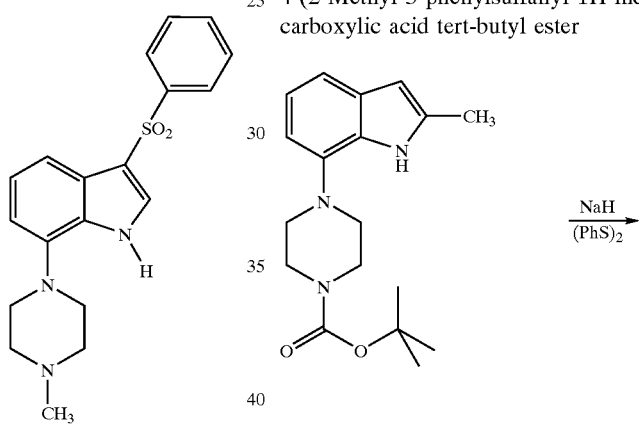

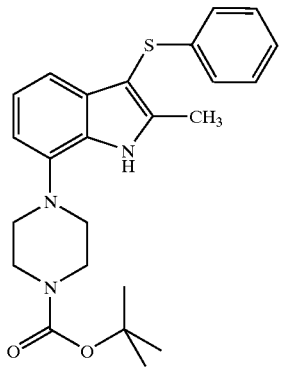

Sodium hydride (0.08 g of 60% dispersion in mineral oil, 1.9 mmol) was added to an ice-cooled solution of 4-(2-methyl-1H-Indol-7-yl)-piperazine-1-carboxylic acid tert-butyl ester (21) prepared as described in Preparation 3 (0.4 g, 1.3 mmol) in 5 mL DMF and the resulting mixture was stirred for 10 min. Phenyl disulfide (0.3 g, 1.4 mmol) was added and the solution was stirred at room temperature for 4 h. Water was added and the mixture was extracted with ethyl acetate. The extract was washed with brine, dried and evaporated to afford 0.5 g of 4-(2-methyl-3-phenylsulfanyl-1H-indol-7-yl)-piperazine-1-carboxylic acid tert-butyl ester) as an oil, $M^+=409$.

Step 2

4-(3-Benzenesulfonyl-2-methyl-1H-indol-7-yl)-piperazine-1-carboxylic acid tert-butyl ester

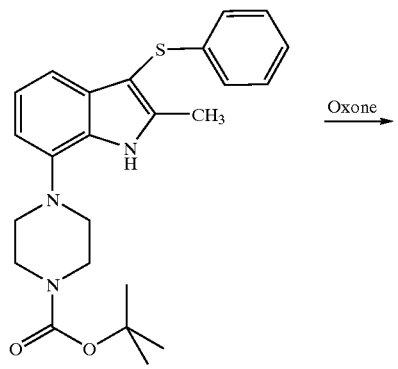

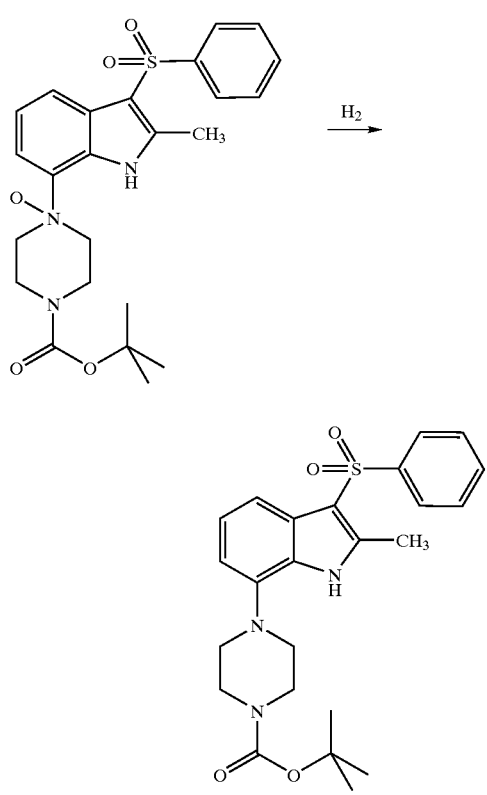

Oxone™ (1.5 g, 2.4 mmol) in 20 mL of water was added to a stirred solution of 4-(2-methyl-3-phenylsulfanyl-1H-indol-7-yl)-piperazine-1-carboxylic acid tert-butyl ester (0.5 g, 1.2 mmol) in 25 mL of methanol. The mixture was stirred for 2 h, diluted with water, and extracted with ethyl acetate. The ethyl acetate was dried (sodium sulfate) and evaporated to afford a solid residue of the sulfone N-oxide. This was dissolved in 50 mL of methanol and hydrogenated at atmospheric pressure over 0.3 g of 10% Pd-C for 12 h. Dichloromethane was added and the mixture was filtered and evaporated. Trituration of the residue with ether afforded 0.25 g of 4-(3-benzenesulfonyl-2-methyl-1H-indol-7-yl)-piperazine-1-carboxylic acid tert-butyl ester as a white solid, m.p. 168–169° C.

Step 3

3-Benzenesulfonyl-2-methyl-7-piperazin-1-yl-1H-indole hydrochloride

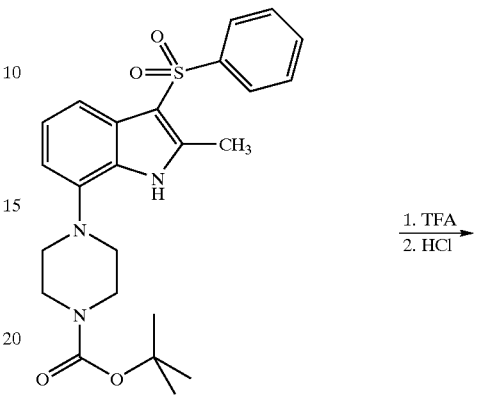

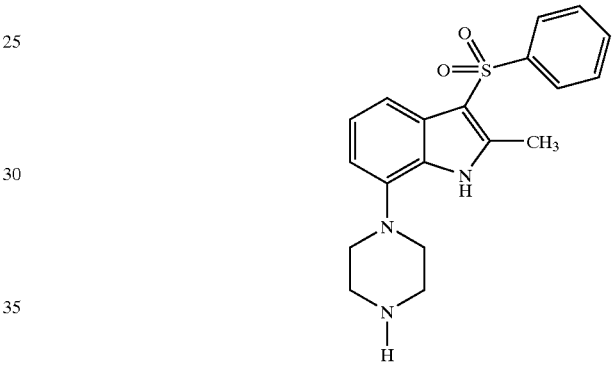

4-(3-Benzenesulfonyl-2-methyl-1H-indol-7-yl)-piperazine-1-carboxylic acid tert-butyl ester (0.25 g) was dissolved in 2 mL of dichloromethane and 2 mL of trifluoroacetic acid was added. After 10 min the mixture was concentrated in vacuo, taken into water, and washed with ether. The aqueous layer was basified with ammonium hydroxide, extracted with dichloromethane, and the extract was dried (sodium sulfate) and evaporated to afford the crude free base which was crystallized from dichloromethane-ether to afford 35 mg of 3-benzenesulfonyl-2-methyl-7-piperazin-1-yl-1H-indole (601), m.p. 188–190° C.

Similarly following the procedure described above but replacing phenyl disulfide in Step 1 with the appropriate substituted phenyl disulfides, the following compounds were prepared:

3-(4-chlorobenzenesulfonyl)-2-methyl-7-piperazin-1-yl-1H-indole (602), m.p. 118–120° C.;

3-(4-fluorobenzenesulfonyl)-2-methyl-7-piperazin-1-yl-1H-indole (603), m.p. 232–236 ° C.; and 3-(4-methoxybenzenesulfonyl)-2-methyl-7-piperazin-1-yl-1H-indole (604), m.p. 182–184 ° C.

Example 7

3-Phenylsulfanyl-7-piperazin-1-yl-1H-indole

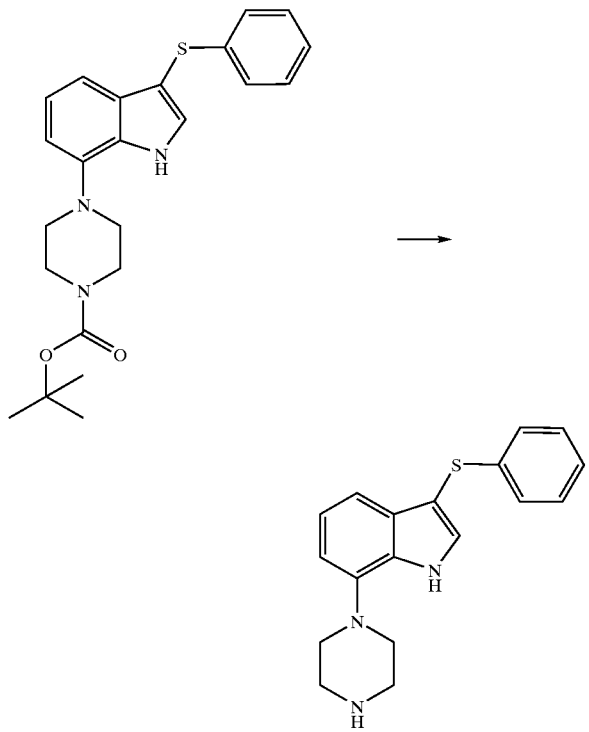

Trifluoroacetic acid (5 mL) was added to a solution of 4-(3-phenylsulfanyl-1H-indol-7-yl)piperazine-1-carboxylic acid tert-butyl ester (700 mg, 1.7 mmol), prepared as described in Example 1 Step 1, in 4 mL of dichloromethane. After 15 min the solution was diluted with water, basified with ammonium hydroxide, and extracted with dichloromethane. The dichloromethane was washed with brine and evaporated to afford 3-phenylsulfanyl-7-piperazin-1-yl-1H-indole (701) as a solid. The hydrochloride salt crystallized from ethanol-HCl to afford 500 mg of white solid, m.p. 300° C. Similarly replacing 4-(3-phenylsulfanyl-1H-indol-7-yl) piperazine-1-carboxylic acid tert-butyl ester with the appropriate sulfanyl derivatives, prepared as described in other examples herein, the following compounds were prepared:

3-(2,3-dichloro-phenylsulfanyl)-5-piperazin-1-yl-1H-indole (702), mp 255.1–255.5° C.; 3-phenylsulfanyl-5-piperazin-1-yl-1H-indole (703), mp. 246–247, and 3-(2,6-dichloro-phenylsulfanyl)-5-piperazin-1-yl-1H-indole (704) M+H=378.

EXAMPLE 8

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

EXAMPLE 9

| Composition for Oral Administration | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

EXAMPLE 10

| Composition for Oral Administration | |
|---|---|
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

EXAMPLE 11

| Parenteral Formulation (IV) | |
|---|---|
| Ingredient | % wt./wt. |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

EXAMPLE 12

| Suppository Formulation | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

EXAMPLE 13

| Topical Formulation | |
|---|---|
| Ingredients | grams |
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Example 14

Nasal Spray Formulations

Several aqueous suspensions containing from about 0.025–0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50–100 microliters of formulation per actuation. A typical dosing schedule is 2–4 sprays every 4–12 hours.

Example 15

Radioligand Binding Studies

The binding activity of compounds of this invention in vitro was determined as follows.

Duplicate determinations of ligand affinity are made by competing for binding of [3H]LSD in cell membranes derived from HEK293 cells stably expressing recombinant human 5-HT6 receptor.

All determinations are made in assay buffer containing 50 mM Tris-HCl, 10 mM MgSO4, 0.5 mM EDTA, 1 mM ascorbic acid, pH 7.4 at 37° C., in a 250 microliter reaction volume. Assay tubes containing [3H] LSD (5 nM), competing ligand, and membrane are incubated in a shaking water bath for 60 min. at 37° C., filtered onto Packard GF-B plates (pre-soaked with 0.3% PEI) using a Packard 96 well cell harvester and washed 3 times in ice cold 50 mM Tris-HCl. Bound [3H] LSD is determined as radioactive counts per minute using Packard TopCount.

Displacement of [3H]LSD from the binding sites was quantified by fitting concentration-binding data to a 4-parameter logistic equation:

$$\text{binding} = \text{basal} + \left( \frac{B\max - \text{basal}}{1 + 10^{-Hill(\log[ligand] - \log IC_{50})}} \right)$$

where Hill is the Hill slope, [ligand] is the concentration of competing radioligand and IC50 is the concentration of radioligand producing half-maximal specific binding of radioligand. The specific binding window is the difference between the Bmax and the basal parameters.

Proceeding as in Example 15, compounds of Formula I were tested and found to be selective 5-HT6 antagonists.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of Formula I:

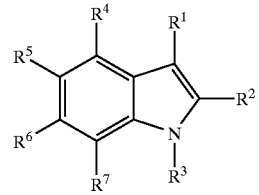

Formula I wherein:

$R^1$ is —S(O)$_{0-2}$—A, —C(O)—A, or —(CH$_2$)$_{0-1}$—A, wherein A is selected from aryl and heteroaryl, said heteroaryl being a monovalent aromatic carbocyclic radical having one or two rings incorporating one, two, or three heteroatoms chosen from nitrogen, oxygen, or sulfur, and said aryl and heteroaryl are each independently in each occurrence optionally substituted with one or more groups selected from hydroxy, cyano, $C_{1-6}$-alkyl, $C_{1-6}$-alkoxy, thio-$C_{1-6}$-alkyl, halo, halo-$C_{1-6}$-alkyl, hydroxy-$C_{1-6}$-alkyl, nitro, $C_{1-6}$-alkoxycarbonyl, $C_{1-6}$-alkylcarbonyl, $C_{1-6}$-alkylsulfonyl, halo-$C_{1-6}$-alkylsulfonyl, amino, $C_{1-6}$-alkylamino, di-$C_{1-6}$-alkylamino, $C_{1-6}$-alkylaminocarbonyl, $C_{1-6}$-alkylcarbonylamino, $C_{1-6}$-alkylaminosulfonyl, and $C_{1-6}$-alkylsulfonylamino;

$R^2$ is selected from hydrogen, $C_{1-6}$-alkyl, $C_{1-6}$-alkoxy, and $C_{1-6}$-alkylthio;

$R^3$ is selected from hydrogen and $C_{1-6}$-alkyl;

$R^4$ is selected from hydrogen, halogen, $C_{1-6}$-alkyl, $C_{1-6}$-alkoxy, $C_{1-6}$-alkylthio, halo-$C_{1-6}$-alkyl, cyano, and $C_{1-6}$-alkylcarbonyl; and one of $R^5$, $R^6$ or $R^7$ is a group of general Formula B, wherein W is or a nitrogen atom, and $R^8$, $R^9$ and $R^{10}$ are each independently selected from hydrogen, $C_{1-10}$-alkyl and benzyl;

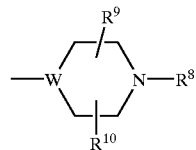

Formula B and the others are each independently of each other selected from hydrogen, halogen, $C_{1-6}$-alkyl, $C_{1-6}$-alkoxy, $C_{1-6}$-alkylthio, haloalkyl, cyano, and $C_{1-6}$-alkylcarbonyl;

or individual isomers, racemic or non racemic mixtures of isomers, prodrugs, or pharmaceutically acceptable salts or solvates thereof.

2. The compound of claim 1, wherein $R^1$ is —$SO_2$—A.

3. The compound of claim 2, wherein A is an aryl group.

4. The compound of claim 2, wherein A is optionally substituted with one or more groups selected from hydroxy, cyano, $C_{1-6}$-alkyl, $C_{1-6}$-alkoxy, thio-$C_{1-6}$-alkyl, halo, halo-$C_{1-6}$-alkyl, hydroxy-$C_{1-6}$-alkyl, nitro, $C_{1-6}$-alkoxycarbonyl, $C_{1-6}$-alkylcarbonyl, $C_{1-6}$-alkylsulfonyl, halo-$C_{1-6}$-alkylsulfonyl, amino, $C_{1-6}$-alkylamino, di-$C_{1-6}$-alkylamino, $C_{1-6}$-alkylaminocarbonyl, $C_{1-6}$-alkylcarbonylamino, $C_{1-6}$-alkylaminosulfonyl, and $C_{1-6}$-alkylsulfonylamino.

5. The compound of claim 1, wherein $R^1$ is —S—A.

6. The compound of claim 5, wherein A is an aryl group.

7. The compound of claim 5, wherein A is phenyl optionally substituted with one or more groups selected from hydroxy, cyano, $C_{1-6}$-alkyl, $C_{1-6}$-alkoxy, thio-$C_{1-6}$-alkyl, halo, halo-$C_{1-6}$-alkyl, hydroxy-$C_{1-6}$-alkyl, nitro, $C_{1-6}$-alkoxycarbonyl, $C_{1-6}$-alkylcarbonyl, $C_{1-6}$-alkylsulfonyl, halo-$C_{1-6}$-alkylsulfonyl, amino, $C_{1-6}$-alkylamino, di-$C_{1-6}$-alkylamino, $C_{1-6}$-alkylaminocarbonyl, $C_{1-6}$-alkylcarbonylamino, $C_{1-6}$-alkylaminosulfonyl, and $C_{1-6}$-alkylsulfonylamino.

8. A compound of Formula I comprising:

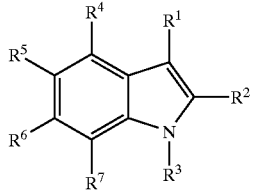

Formula I wherein:

$R^1$ is —$SO_{0-2}$—A, —C(O)—A, or —$(CH_2)_{0-1}$—A, wherein A is aryl or heteroaryl, said heteroaryl being monovalent aromatic carbocyclic radical having one or two rings incorporating one, two, or three heteroatoms chosen from nitrogen, oxygen, or sulfur; said aryl and heteroaryl are each independently in each occurrence optionally substituted with one or more groups selected from hydroxy, cyano, $C_{1-6}$-alkyl, $C_{1-6}$-alkoxy, thio-$C_{1-6}$-alkyl, halo, halo-$C_{1-6}$-alkyl, hydroxy-$C_{1-6}$-alkyl, nitro, $C_{1-6}$-alkoxycarbonyl, $C_{1-6}$-alkylcarbonyl, $C_{1-6}$-alkylsulfonyl, halo-$C_{1-6}$-alkylsulfonyl, amino, $C_{1-6}$-alkylamino, di-$C_{1-6}$-alkylamino, $C_{1-6}$-alkylaminocarbonyl, $C_{1-6}$-alkylcarbonylamino, $C_{1-6}$-alkylaminosulfonyl, and $C_{1-6}$-alkylsulfonylamino;

$R^2$ is selected from hydrogen, $C_{1-6}$-alkyl, $C_{1-6}$-alkoxy, and $C_{1-6}$-alkylthio;

$R^3$ is selected from hydrogen and $C_{1-6}$-alkyl;

$R^7$ is a group of general Formula B, wherein W is a nitrogen atom, and $R^8$, $R^9$ and $R^{10}$ are each independently selected from hydrogen and $C_1$-$C_{10}$-alkyl;

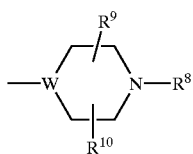

Formula B and $R^4$, $R^5$ and $R^6$ are each independently of each other selected from hydrogen, halogen, $C_{1-6}$-alkyl, $C_{1-6}$-alkylthio, halo-$C_{1-6}$-alkyl, cyano, and $C_{1-6}$-alkylcarbonyl;

or individual isomers, racemic or non racemic mixtures of isomers, prodrugs, or pharmaceutically acceptable salts or solvates thereof.

9. The compound of claim 8, wherein $R^1$ is —$SO_2$—A.

10. The compound of claim 9, wherein A is aryl, optionally substituted with one or more groups selected from hydroxy, cyano, $C_{1-6}$-alkyl, $C_{1-6}$-alkoxy, thio-$C_{1-6}$-alkyl, halo, halo-$C_{1-6}$-alkyl, hydroxy-$C_{1-6}$-alkyl, nitro, $C_{1-6}$-alkoxycarbonyl, $C_{1-6}$-alkylcarbonyl, $C_{1-6}$-alkylsulfonyl, halo-$C_{1-6}$-alkylsulfonyl, amino, $C_{1-6}$-alkylamino, di-$C_{1-6}$-alkylamino, $C_{1-6}$-alkylaminocarbonyl, $C_{1-6}$-alkylcarbonylamino, $C_{1-6}$-alkylaminosulfonyl, and $C_{1-6}$-alkylsulfonylamino.

11. The compound of claim 9, wherein A is phenyl optionally substituted with one or more groups selected from hydroxy, cyano, $C_{1-6}$-alkyl, $C_{1-6}$-alkoxy, thio-$C_{1-6}$-alkyl, halo, halo-$C_{1-6}$-alkyl, hydroxy-$C_{1-6}$-alkyl, nitro, $C_{1-6}$-alkoxycarbonyl, $C_{1-6}$-alkylcarbonyl, $C_{1-6}$-alkylsulfonyl, halo-$C_{1-6}$-alkylsulfonyl, amino, $C_{1-6}$-alkylamino, di-$C_{1-6}$-alkylamino, $C_{1-6}$-alkylaminocarbonyl, $C_{1-6}$-alkylcarbonylamino, $C_{1-6}$-alkylaminosulfonyl, and $C_{1-6}$-alkylsulfonylamino.

12. The compound of claim 9, wherein A is heteroaryl, said heteroaryl being a monovalent aromatic carbocyclic radical having one or two rings incorporating one, two, or three heteroatoms chosen from nitrogen, oxygen, or sulfur, said heteroaryl optionally substituted with one or more groups selected from hydroxy, cyano, $C_{1-6}$-alkyl, $C_{1-6}$-alkoxy, thio-$C_{1-6}$-alkyl, halo, halo-$C_{1-6}$-alkyl, hydroxy-$C_{1-6}$-alkyl, nitro, $C_{1-6}$-alkoxycarbonyl, $C_{1-6}$-alkylcarbonyl, $C_{1-6}$-alkylsulfonyl, halo-$C_{1-6}$-alkylsulfonyl, amino, $C_{1-6}$-alkylamino, di-$C_{1-6}$-alkylamino, $C_{1-6}$-alkylaminocarbonyl, $C_{1-6}$-alkylcarbonylamino, $C_{1-6}$-alkylaminosulfonyl, and $C_{1-6}$-alkylsulfonylamino.

13. The compound of claim 9, wherein A is pyridinyl or benzothiazolyl, said pyridinyl or benzothiazolyl being each independently of each other optionally substituted with one or more groups selected from hydroxy, cyano, $C_{1-6}$-alkyl, $C_{1-6}$-alkoxy, thio-$C_{1-6}$-alkyl, halo, halo-$C_{1-6}$-alkyl, hydroxy-$C_{1-6}$-alkyl, nitro, $C_{1-6}$-alkoxycarbonyl, $C_{1-6}$-alkylcarbonyl, $C_{1-6}$-alkylsulfonyl, halo-$C_{1-6}$-alkylsulfonyl, amino, $C_{1-6}$-alkylamino, di-$C_{1-6}$-alkylamino, $C_{1-6}$-alkylaminocarbonyl, $C_{1-6}$-alkylcarbonylamino, $C_{1-6}$-alkylaminosulfonyl, and $C_{1-6}$-alkylsulfonylamino.

14. The compound of claim 8, wherein $R^1$ is —S—A.

15. The compound of claim 14, wherein A is aryl, optionally substituted with one or more groups selected from hydroxy, cyano, $C_{1-6}$-alkyl, $C_{1-6}$-alkoxy, thio-$C_{1-6}$-alkyl, halo, halo-$C_{1-6}$-alkyl, hydroxy-$C_{1-6}$-alkyl, nitro, $C_{1-6}$-alkoxycarbonyl, $C_{1-6}$-alkylcarbonyl, $C_{1-6}$-alkylsulfonyl, halo-$C_{1-6}$-alkylsulfonyl, amino, $C_{1-6}$-alkylamino, di-$C_{1-6}$-alkylamino, $C_{1-6}$-alkylaminocarbonyl, $C_{1-6}$-alkylcarbonylamino, $C_{1-6}$-alkylaminosulfonyl, and $C_{1-6}$-alkylsulfonylamino.

16. The compound of claim 14, wherein A is phenyl optionally substituted with one or more optionally substituted with one or more groups selected from hydroxy, cyano, $C_{1-6}$-alkyl, $C_{1-6}$-alkoxy, thio-$C_{1-6}$-alkyl, halo, halo-$C_{1-6}$-alkyl, hydroxy-$C_{1-6}$-alkyl, nitro, $C_{1-6}$-alkoxycarbonyl, $C_{1-6}$-alkylcarbonyl, $C_{1-6}$-alkylsulfonyl, halo-$C_{1-6}$-alkylsulfonyl, amino, $C_{1-6}$-alkylamino, di-$C_{1-6}$-alkylamino, $C_{1-6}$-alkylaminocarbonyl, $C_{1-6}$-alkylcarbonylamino, $C_{1-6}$-alkylaminosulfonyl, and $C_{1-6}$-alkylsulfonylamino.

17. A compound of Formula I comprising:

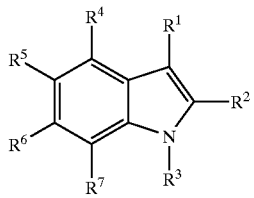

Formula I wherein:
R¹ is —S(O)₀₋₂—A, —C(O)—A, or —(CH₂)₀₋₁—A, wherein A is aryl or heteroaryl, said heteroaryl being a monovalent aromatic carbocyclic radical having one or two rings incorporating one, two, or three heteroatoms chosen from nitrogen, oxygen, or sulfur; and said aryl and heteroaryl are each independently of each other in each occurrence optionally substituted with one or more groups selected from hydroxy, cyano, C₁₋₆-alkyl, C₁₋₆-alkoxy, thio-C₁₋₆-alkyl, halo, halo-C₁₋₆-alkyl, hydroxy-C₁₋₆-alkyl, nitro, C₁₋₆-alkoxycarbonyl, C₁₋₆-alkylcarbonyl, C₁₋₆-alkylsulfonyl, halo-C₁₋₆-alkylsulfonyl, amino, C₁₋₆-alkylamino, di-C₁₋₆-alkylamino, C₁₋₆-alkylaminocarbonyl, C₁₋₆-alkylcarbonylamino, C₁₋₆-alkylaminosulfonyl, and C₁₋₆-alkylsulfonylamino;

R² is selected from hydrogen, C₁₋₆-alkyl, C₁₋₆-alkoxy, and C₁₋₆-alkylthio;

R³ is selected from hydrogen and C₁₋₆-alkyl;

R⁵ is a group of general formula B, wherein W is a nitrogen atom, and R⁸, R⁹ and R¹⁰ are each independently selected from hydrogen and C₁₋₁₀-alkyl;

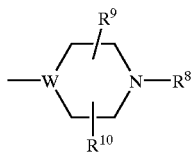

Formula B and R⁴, R⁶ and R⁷ are each independently of each other selected from hydrogen, halogen, C₁₋₆-alkyl, C₁₋₆-alkoxy, C₁₋₆-alkylthio, halo-C₁₋₆-alkyl, cyano, and alkylcarbonyl;

or individual isomers, racemic or non racemic mixtures of isomers, prodrugs, or pharmaceutically acceptable salts or solvates thereof.

18. The compound of claim 17, wherein R¹ is —SO₂—A.
19. The compound of claim 18, wherein A is aryl.
20. The compound of claim 18, wherein A is phenyl optionally substituted with one or more optionally substituted with one or more groups selected from hydroxy, cyano, C₁₋₆-alkyl, C₁₋₆-alkoxy, thio-C₁₋₆-alkyl, halo, halo-C₁₋₆-alkyl, hydroxy-C₁₋₆-alkyl, nitro, C₁₋₆-alkoxycarbonyl, C₁₋₆-alkylcarbonyl, C₁₋₆-alkylsulfonyl, halo-C₁₋₆-alkylsulfonyl, amino, C₁₋₆-alkylamino, di-C₁₋₆-alkylamino, C₁₋₆-alkylaminocarbonyl, C₁₋₆-alkylcarbonylamino, C₁₋₆-alkylaminosulfonyl, and C₁₋₆-alkylsulfonylamino.

21. The compound of claim 17, wherein R¹ is —S—A.
22. The compound of claim 21, wherein A is aryl, optionally substituted with one or more groups selected from hydroxy, cyano, C₁₋₆-alkyl, C₁₋₆-alkoxy, thio-C₁₋₆-alkyl, halo, halo-C₁₋₆-alkyl, hydroxy-C₁₋₆-alkyl, nitro, C₁₋₆-alkoxycarbonyl, C₁₋₆-alkylcarbonyl, C₁₋₆-alkylsulfonyl, halo-C₁₋₆-alkylsulfonyl, amino, C₁₋₆-alkylamino, di-C₁₋₆-alkylamino, C₁₋₆-alkylaminocarbonyl, C₁₋₆-alkylcarbonylamino, C₁₋₆-alkylaminosulfonyl, and C₁₋₆-alkylsulfonylamino.

23. The compound of claim 21, wherein A is phenyl optionally substituted with one or more groups selected from hydroxy, cyano, C₁₋₆-alkyl, C₁₋₆-alkoxy, thio-C₁₋₆-alkyl, halo, halo-C₁₋₆-alkyl, hydroxy-C₁₋₆-alkyl, nitro, C₁₋₆-alkoxycarbonyl, C₁₋₆-alkylcarbonyl, C₁₋₆-alkylsulfonyl, halo-C₁₋₆-alkylsulfonyl, amino, C₁₋₆-alkylamino, di-C₁₋₆-alkylamino, C₁₋₆-alkylaminocarbonyl, C₁₋₆-alkylcarbonylamino, C₁₋₆-alkylaminosulfonyl, and C₁₋₆-alkylsulfonylamino.

24. The compound of claim 8, wherein the compound is:
3-benzenesulfonyl-7-piperazin-1-yl-1H-indole;
3-benzenesulfonyl-1-methyl-7-piperazin-1-yl-1H-indole;
3-benzenesulfonyl-2-methyl-7-piperazin-1-yl-1H-indole;
3-(4-chlorobenzenesulfonyl)-2-methyl-7-piperazin-1-yl-1H-indole;
3-(4-methoxybenzenesulfonyl)-2-methyl-7-piperazin-1-yl-1H-indole;
7-piperazin-1-yl-3-(pyridine-4-sulfonyl)-1H-indole;
7-piperazin-1-yl-3-(pyridine-2-sulfonyl)-1H-indole;
1-methyl-7-piperazin-1-yl-3-(pyridine-2-sulfonyl)-1H-indole;
3-benzenesulfonyl-7-(4-methyl-piperazin-1-yl)-1H-indole;
3-(3,4-dichloro-benzenesulfonyl)-7-piperazin-1-yl-1H-indole;
2-(7-piperazin-1-yl-1H-indole-3-sulfonyl)-benzothiazole;
3-(4-fluoro-benzenesulfonyl)-2-methyl-7-piperazin-1-yl-1H-indole;
3-(4-fluoro-benzenesulfonyl)-7-piperazin-1-yl-1H-indole;
7-piperazin-1-yl-3-(toluene-4-sulfonyl)-1H-indole;
3-(3,5-dichloro-benzenesulfonyl)-7-piperazin-1-yl-1H-indole;
3-(3-chloro-benzenesulfonyl)-7-piperazin-1-yl-1H-indole;
3-(2-chloro-benzenesulfonyl)-7-piperazin-1-yl-1H-indole;
7-piperazin-1-yl-3-(2-trifluoromethyl-benzenesulfonyl)-1H-indole;
1-methyl-7-piperazin-1-yl-3-(2-trifluoromethyl-benzenesulfonyl)-1H-indole;
3-(4-fluoro-benzenesulfonyl)-1-methyl-7-piperazin-1-yl-1H-indole;
1-methyl-7-piperazin-1-yl-3-(pyridine-2-sulfonyl)-1H-indole;
1-methyl-7-piperazin-1-yl-3-(3-trifluoromethyl-benzenesulfonyl)-1H-indole;
3-(2-chloro-benzenesulfonyl)-1-methyl-7-piperazin-1-yl-1H-indole;
3-(3-chloro-benzenesulfonyl)-1-methyl-7-piperazin-1-yl-1H-indole;
3-benzenesulfonyl-1-methyl-7-(4-methyl-piperazin-1-yl)-1H-indole;
3-(3,4-dichloro-benzenesulfonyl)-7-(4-methyl-piperazin-1-yl)-1H-indole;
3-(2-chloro-benzenesulfonyl)-7-(4-methyl-piperazin-1-yl)-1H-indole;
3-(3-chloro-benzenesulfonyl)-7-(4-methyl-piperazin-1-yl)-1H-indole;
3-(2,4-dichloro-benzenesulfonyl)-7-(4-methyl-piperazin-1-yl)-1H-indole;
3-(3,5-dichloro-benzenesulfonyl)-7-(4-methyl-piperazin-1-yl)-1H-indole;
7-(4-methyl-piperazin-1-yl)-3-(2-trifluoromethyl-benzenesulfonyl)-1H-indole;
3-phenylsulfanyl-7-piperazin-1-yl-1H-indole;
or an individual isomer, racemic or non-racemic mixture of isomers, or pharmaceutically acceptable salt or solvate thereof.

25. The compound of claim 17, wherein the compound is:
3-benzenesulfonyl-5-piperazin-1-yl-1H-indole;
3-benzenesulfonyl-1-methyl-5-piperazin-1-yl-1H-indole;
3-(2,3-dichloro-phenylsulfanyl)-5-piperazin-1-yl-1H-indole;
3-(2,3-dichloro-benzenesulfonyl)-5-piperazin-1-yl-1H-indole;
3-(2,3-dichloro-benzenesulfonyl)-1-methyl-5-piperazin-1-yl-1H-indole;
1-methyl-5-piperazin-1-yl-3-(3-trifluoromethyl-benzenesulfonyl)-1H-indole;
5-piperazin-1-yl-3-(4-trifluoromethyl-benzenesulfonyl)-1H-indole;
3-(4-chloro-benzenesulfonyl)-5-piperazin-1-yl-1H-indole;
3-(3,5-dichloro-benzenesulfonyl)-5-piperazin-1-yl-1H-indole;
3-(3,5-dichloro-benzenesulfonyl)-1-methyl-5-piperazin-1-yl-1H-indole;
3-phenylsullfanyl-5-piperazin-1-yl-1H-indole;
3-(2-chloro-benzenesulfonyl)-5-piperazin-1-yl-1H-indole;
3-(4-fluoro-benzenesulfonyl)-5-piperazin-1-yl-1H-indole;
3-(4-fluoro-benzenesulfonyl)-1-methyl-5-piperazin-1-yl-1H-indole;
3-(2-chloro-benzenesulfonyl)-1-methyl-5-piperazin-1-yl-1H-indole;
or an individual isomer, racemic or non-racemic mixture of isomers, or pharmaceutically acceptable salt or solvate thereof.

26. A pharmaceutical composition comprising a therapeutically effective amount of at least one compound of claim 1 in admixture with at least one pharmaceutically acceptable carrier.

27. A process for preparing a compound as claimed in claim 1, said process comprising
i) reacting a compound having a general Formula 4

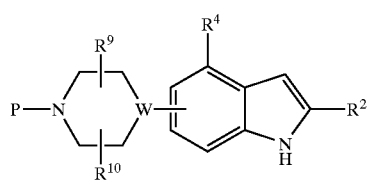

wherein P is a protecting group and $R^2$, $R^4$, $R^9$ and $R^{10}$ are as defined in claim 1, with a compound of general formula $(A—S)_2$, wherein A is aryl or heteroaryl'
ii) optional alkylation of the nitrogen of the indole group,
iii) removal of the protecting group P;
to provide a compound of Formula I,

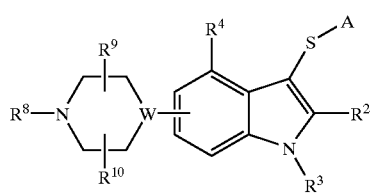

wherein $R^8$ is hydrogen, and A, $R^2$, $R^3$, $R^4$, $R^9$, and $R^{10}$ are as defined in claim 1, and
iv) optional alkylation to provide a compound of the general Formula I, wherein $R^8$ is $C_{1-10}$-alkyl, and A, $R^2$, $R^3$, $R^4$, $R^9$, and $R^{10}$ are as defined in claim 1.

28. A process for preparing a compound as claimed in claim 1 which comprises
i) reacting a compound having a general Formula 4

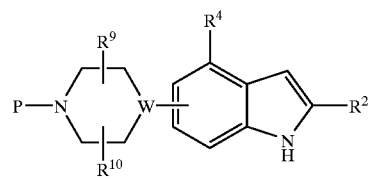

wherein P is a protecting group and $R^2$, $R^4$, $R^9$ and $R^{10}$ are as defined in claim 1 with a compound of general formula $(A—S)_2$, wherein A is aryl or heteroaryl, to provide an adduct 4a

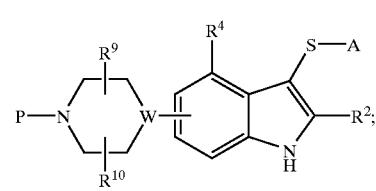

ii) oxidation of the sulfur atom of 4a;
iii) optional alkylation of the nitrogen of the indole group of oxidized 4a;
iv) removal of the protecting group P;
to provide a compound of Formula I,

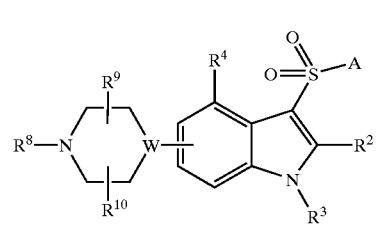

wherein $R^8$ is hydrogen, and A, $R^2$, $R^3$, $R^4$, $R^9$, and $R^{10}$ are as defined in claim 1, and
v) optional alkylation of the nitrogen of the piperazine or piperidine group to provide a compound of the general Formula I, wherein $R^8$ is $C_{1-10}$-alkyl, and A, $R^2$, $R^3$, $R^4$, $R^9$, and $R^{10}$ are as defined in claim 1.

29. A process for preparing a compound as claimed in claim 1, said process comprising
i) reacting 1-halo-2-nitrobenzene with a halomethanesulfonyl benzene to provide a 1-benzenesulfonylmethyl-2-nitrobenzene
ii) amination of the 1-benzenesulfonylmethyl-2-nitrobenzene with a 1-alkylpiperazine to provide a piperazinylated nitrobenzene;
iii) reduction of the nitro group of the piperazinylated nitrobenzene, and iv) addition of an orthoformate, followed by cyclization to yield a compound of Formula 18a,

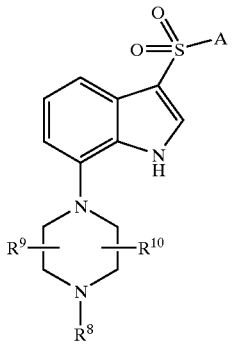

18a wherein $R^8$ is $C_{1-10}$-alkyl and A, $R^9$, and $R^{10}$ are as defined in the summary of the invention.

30. A process for preparing a compound of claim 1, said process comprising i) reacting a compound having a general Formula 4

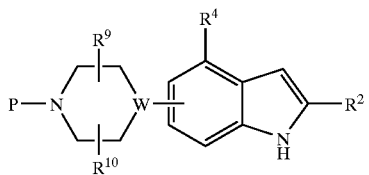

4 wherein P is a protecting group and $R^2$, $R^4$, $R^9$ and $R^{10}$ are as defined in claim 1 with a compound of general formula $(A-S)_2$, wherein A is aryl or heteroaryl, to provide an adduct 4a

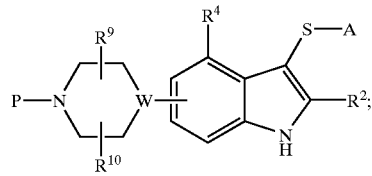

4a ii) oxidation of the sulfur atom of 4a;
iii) optional alkylation of the nitrogen of the indole group of oxidized 4a;
iv) removal of the protecting group P;
to provide a compound of Formula I,

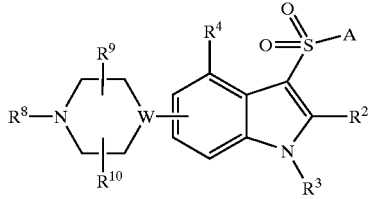

Formula I wherein $R^8$ is hydrogen, and A, $R^2$, $R^3$, $R^4$, $R^9$, and $R^{10}$ are as defined as claim 1, and v) optional alkylation of the nitrogen of the piperazine or piperidine group to provide a compound of the general Formula I, wherein $R^8$ is $C_{1-10}$-alkyl, and A, $R^2$, $R^3$, $R^4$, $R^9$, and $R^{10}$ are as defined in claim 1.

31. A method of treating a subject that has a disease state selected from schizophrenia, depression, memory disorders, attention deficit disorder, and Alzheimer's disease wherein said method comprises administering to said subject a therapeutically effective amount of the compound of claim 1.

32. A method for treating a subject that has a disorders of the gastrointestinal tract, said method comprising administering to said subject a therapeutically effective amount of the compound of claim 1.

* * * * *

UNITED STATES PATENT AND TRADEMARK OFFICE
CERTIFICATE OF CORRECTION

PATENT NO. : 6,787,535 B2
DATED : September 7, 2004
INVENTOR(S) : Colin Charles Beard et al.

It is certified that error appears in the above-identified patent and that said Letters Patent is hereby corrected as shown below:

Column 48,
Line 49, "wherein W is or a nitrogen atom," should read -- wherein W is a nitrogen atom, --;

Column 51,
Lines 46-47, "cyano, and alkylcarbonyl;" should read -- cyano, and $C_{1-6}$-alkylcarbonyl; --;

Column 53,
Line 19, "3-phenylsullfanyl-5-piperazin-1-yl-1H-indole;" should read -- 3-phenylsulfanyl-5-piperazin-1-yl-1H-indole; --;

Column 54,
Lines 1-2, "28. A process for preparing a compound as claimed in claim 1 which comprises" should read -- 28. A process for preparing a compound of Claim 1, said process comprising --;

Column 55,
Lines 23-24, "30. A process for preparing a compound of claim 1, said process comprising" should read -- A process for preparing a compound as claimed in Claim 1 which comprises --;

Column 56,
Line 37, "that has a disorders of" should read -- that has a disorder of --.

Signed and Sealed this

Thirteenth Day of September, 2005

JON W. DUDAS
*Director of the United States Patent and Trademark Office*